US012661147B2

(12) United States Patent
Burgett et al.

(10) Patent No.: US 12,661,147 B2
(45) Date of Patent: Jun. 23, 2026

(54) DEVICES, SYSTEMS, AND METHODS FOR ANALYTE SENSING

(71) Applicant: MEDTRONIC MINIMED, INC., Northridge, CA (US)

(72) Inventors: James E. Burgett, Maple Grove, MN (US); Alford L. McLevish, Roseville, MN (US)

(73) Assignee: Medtronic MiniMed, Inc., Northridge, CA (US)

( * ) Notice: Subject to any disclaimer, the term of this patent is extended or adjusted under 35 U.S.C. 154(b) by 730 days.

(21) Appl. No.: 18/062,367

(22) Filed: Dec. 6, 2022

(65) Prior Publication Data

US 2023/0240714 A1 Aug. 3, 2023

Related U.S. Application Data

(60) Provisional application No. 63/267,460, filed on Feb. 2, 2022.

(51) Int. Cl.
*A61B 5/145* (2006.01)
*A61B 5/00* (2006.01)
*A61B 17/34* (2006.01)

(52) U.S. Cl.
CPC ........ *A61B 17/3468* (2013.01); *A61B 5/0002* (2013.01); *A61B 5/14503* (2013.01); *A61B 5/14532* (2013.01); *A61B 5/6849* (2013.01)

(58) Field of Classification Search
CPC .............. A61B 17/3468; A61B 5/0002; A61B 5/14503; A61B 5/14532; A61B 5/14865; A61B 5/6833; A61B 5/6849
See application file for complete search history.

(56) References Cited

U.S. PATENT DOCUMENTS

| | | |
|---|---|---|
| 2017/0290533 A1 | 10/2017 | Antonio et al. |
| 2018/0116570 A1 | 5/2018 | Simpson et al. |
| 2021/0038131 A1 | 2/2021 | Li et al. |
| 2021/0052301 A1 | 2/2021 | Gass et al. |
| 2021/0186425 A1 | 6/2021 | Rodriguez et al. |
| 2021/0228156 A1* | 7/2021 | Kouge ................. H05K 5/0086 |

* cited by examiner

*Primary Examiner* — Eric J Messersmith
(74) *Attorney, Agent, or Firm* — Fortem IP LLP

(57) ABSTRACT

Analyte sensors and associated insertion devices are disclosed herein. According to some embodiments, the present technology includes a sensor applicator comprising a housing having an insertion end configured to be positioned at or adjacent a user's skin at an insertion site, a needle carried by the housing and configured for insertion into the user's skin at the insertion site, and a sensor assembly comprising a base and a sensing portion extending from the base. The base is supported by the housing in a first position during insertion of the needle and configured to rotate into a second, laid-flat position on the user's skin after removal of the housing from the insertion site.

15 Claims, 16 Drawing Sheets

DEVICES, SYSTEMS, AND METHODS FOR ANALYTE SENSING

CROSS-REFERENCE TO RELATED APPLICATIONS

This application claims the benefit of priority to U.S. Provisional Application No. 63/267,460, filed Feb. 2, 2022, which is incorporated herein by reference in its entirety.

TECHNICAL FIELD

The present technology relates generally to devices for inserting a needle into the skin of a mammalian subject.

BACKGROUND

Diabetes is a disease in which the body does not produce or properly use insulin. Millions of people in the United States and around the world have been diagnosed with some form of diabetes. Type 1 diabetes results from the body's failure to produce insulin. Type 2 diabetes results from insulin resistance in which the body fails to properly use insulin. In order to effectively manage the disease, diabetics must closely monitor and manage their blood glucose levels through exercise, diet, and medications. In particular, both Type 1 and Type 2 diabetics rely on insulin delivery and blood glucose monitoring to control their diabetes.

Monitoring blood glucose levels plays an integral role in the management and control of diabetes. Finger stick measurements, glucose sensors and monitors have traditionally been used to check the blood glucose levels of diabetic patients. In recent years, continuous glucose monitoring systems have been developed utilizing the latest sensor technologies incorporating both implantable and external sensors. Newer systems deliver the preciseness of finger stick measurements coupled with the convenience of not having to repeatedly prick the skin to obtain glucose measurements. These newer systems provide the equivalent of over 200 finger stick readings per day. Additionally, continuous glucose monitoring systems allow physicians and patients to monitor blood glucose trends of their body and suggest and deliver insulin based on each patient's particular needs. Accordingly, physicians and medical device companies are always searching for more convenient ways to keep diabetic patients aware of their blood glucose levels throughout the day.

As such, analyte sensors may be generally used to test analyte levels in patients. For example, thin film sensors may be used for obtaining an indication of blood glucose levels and monitoring blood glucose levels in a diabetic patient. In these instances, a portion of a glucose sensor is positioned subcutaneously in direct contact with patient extracellular fluid. To insert a glucose sensor subcutaneously, an insertion device is used that quickly injects the sensor into the patient's skin and simultaneously adheres the monitor to the patient's skin. Glucose sensors need to be changed every few days, and whenever the sensor stops working, is damaged, or is giving erroneous readings. Therefore, a diabetic patient often carries an extra sensor with them. However, these insertion devices are often large and cumbersome to carry around.

Once a continuous glucose sensor is inserted, the continuous glucose sensor is designed to monitor a glucose concentration of the patient and a sensor signal is produced that is representative of the glucose concentration. The continuous glucose sensor may use wireless data communication techniques to transmit data indicative of the blood glucose levels to a receiving device such as a portable infusion pump, a glucose monitor device, and/or the like. For example, the transmitted sensor signal may be used to generate a controller input for a controller to generate commands that affect the operation of a delivery system to infuse a liquid, which includes insulin, into the patient. The various components necessary to enable the data management and communications adds to the size of the glucose sensor assembly, and thus the size of the insertion device.

SUMMARY

The present technology is illustrated, for example, according to various aspects described below. These various aspects are provided as examples and do not limit the subject technology.

According to several embodiments of the present technology, a device comprises a sensor assembly including a base and a sensing portion extending from the base. The base is configured to be positioned on a user's skin and the sensing portion is configured to be positioned at a subcutaneous location. The base has a long dimension and a short dimension. The support is coupled to the sensor assembly and has top and bottom surfaces. The bottom surface is configured to be adhered to a patient's skin and the top surface is configured to receive the base of the sensor assembly thereon. The support has a long dimension and a short dimension. The device is moveable between an insertion position and a wearable position. In the insertion position, the long dimension of the base is angled relative to the long dimension of the support. In the wearable position, the long dimension of the base is substantially parallel to the long dimension of the support. In some embodiments, in the insertion position, the long dimension of the base is substantially perpendicular to the long dimension of the support. According to several embodiments, the device is configured to be carried by an applicator in the insertion position, and wherein the device is configured such that removal of device from the applicator causes the base to rotate into alignment with the support. In some embodiments, the sensing portion is connected to the base via an extension that is configured to bend, fold, and/or coil along its longitudinal axis. According to certain embodiments, the base is configured to rotate over the extension into the wearable position such that the extension is disposed between the base and the patient's skin. The base can comprise a transmitter configured to wirelessly communicate with a remote infusion pump and/or monitor device. The sensor assembly can be configured to detect blood glucose levels.

Several embodiments of the present disclosure comprise a sensor including a base having a top surface and a bottom surface, a sensing portion extending from the base, and an extension configured to bend, fold, and/or coil along its longitudinal axis. The extension couples the sensing portion to the base. The base is configured to be positioned on a user's skin and the sensing portion is configured to be positioned at a subcutaneous location. The base is moveable between an insertion position and a wearable position. In the insertion position, the bottom surface of the base is angled relative to the user's skin. In the wearable position, the bottom surface of the base is substantially parallel to and adhered to of the user's skin and the extension bends, folds and/or coils along its longitudinal axis between the bottom surface of the base and the user's skin.

Several methods of the present technology for inserting a portion of a sensor assembly in a human body comprise positioning a portion of an applicator at a patient's skin at an intended sensor insertion site, wherein the applicator includes a sensor assembly comprising a base and a sensing portion extending from the base. The method includes inserting the sensing portion into the patient's skin, where the base is supported by the applicator in a first position during insertion of the sensing portion. The method further includes rotating the base from the first position to a second position in which the base resides on the patient's skin in a laid-flat orientation. In some embodiments, the method can further comprise removing the applicator from the insertion site, thereby exposing the base while in the first position. According to several embodiments, rotation of the base from the first position to the second position is automatically triggered by removal of the applicator. In some embodiments, when the base is in the first position, a long axis of the base is oriented substantially perpendicular to the skin surface. According to several methods, the applicator further comprises a needle and the sensing portion is coupled to the needle. After inserting the sensing portion into the patient's skin, the method further comprises moving the needle from an extended position in which a distal end of the needle projects from the housing to a retracted position in which the distal end is positioned within the housing. According to some embodiments, the method comprises inserting the sensing portion into the patient's skin occurs along an insertion path. During insertion of the sensing portion, a long axis of the base is substantially parallel to the to the insertion path when the base is in the first position. In several embodiments, the method comprises measuring blood glucose levels via the sensor assembly after the base is rotated to the laid-flat position on the skin. The sensing portion can be connected to the base via an extension that is configured to bend, fold, and/or coil along its longitudinal axis. In some embodiments, inserting the sensing portion causes the extension to bend, fold, and/or coil along its longitudinal axis. According to several embodiments, the base rotates over the extension such that the extension is between the base and the patient's skin.

According to several embodiments of the present technology, a sensor applicator comprises a housing having an insertion end configured to be positioned at or adjacent a user's skin at an insertion site, and a needle carried by the housing and configured for insertion into the user's skin at the insertion site. The applicator includes a sensor assembly comprising a base and a sensing portion extending from the base, wherein the base is supported by the housing in a first position during insertion of the needle and configured to rotate into a second, laid-flat position on the user's skin after removal of the housing from the insertion site. In some embodiments, the sensing portion of the sensor assembly is coupled to the needle such that subcutaneous insertion of the needle causes subcutaneous insertion of the sensing portion. According to several embodiments, the base is disposed laterally adjacent the needle such that an insertion path of the needle does not intersect any portion of the base. In some embodiments, the needle has a distal end configured to be inserted through the skin of the user. The needle can be movable between a pre-insertion position in which the distal end is retracted relative to the insertion end of the housing, and an extended position in which the distal end projects relative to the insertion end. In some embodiments, the insertion end of the applicator is configured to engage an adhesive pad positioned on the skin at the insertion site. According to several embodiments, the applicator includes a spring configured to move the needle from a pre-insertion position within the housing to an extended position in which a distal end of the needle projects from the insertion end of the housing. In certain embodiments, the applicator includes a spring configured to move the needle from an extended position in which a distal end of the needle projects from the insertion end of the housing to a retracted position in which the distal end of the needle is within the housing. In some embodiments, when the base is in the first position, a long axis of the base is substantially parallel to an insertion path of the needle. In some embodiments, when the base is in the first position, a long axis of the base is substantially perpendicular to the user's skin. According to certain embodiments, the sensor assembly is configured to measure blood glucose levels after the base is rotated to the second, laid-flat position on the skin. In several embodiments, the sensing portion is connected to the base via an extension that is configured to bend, fold, and/or coil along its longitudinal axis. In some embodiments, base is configured to rotate over the extension into the second, laid-flat position such that the extension is disposed between the base and the patient's skin. The applicator can comprise a transmitter configured to wirelessly communicate with a remote infusion pump and/or monitor device. The sensor assembly can comprise an integrated transmitter configured to wirelessly communicate with a remote infusion pump and/or monitor device. In some embodiments, when the base is in the first position, the base has a first end proximate the insertion end of the housing and a second end. The sensor assembly can comprise a spring-loaded hinge at the first end of the base such that, when the housing is removed from the insertion site, the base automatically rotates from the first position to the second position.

According to several embodiments of the present technology, a sensor applicator comprises a housing having an insertion end configured to be positioned at or adjacent a user's skin at an insertion site, and a needle carried by the housing and configured for insertion into the user's skin at the insertion site. The applicator further includes a sensor assembly comprising a base and a sensing portion extending from the base. The base has a first end and a second end along its long axis. The base is supported by the housing in a first orientation during insertion of the needle in which the first end of the base is adjacent the user's skin and the second end is spaced apart from the user's skin by a distance equivalent to a length of the long axis of the base. The base is configured to move into a second orientation after removal of the housing from the insertion site in which both the first and second ends are adjacent the user's skin.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

In FIG. 4A, the applicator assembly is in a pre-insertion state.

DETAILED DESCRIPTION

Figure 1:
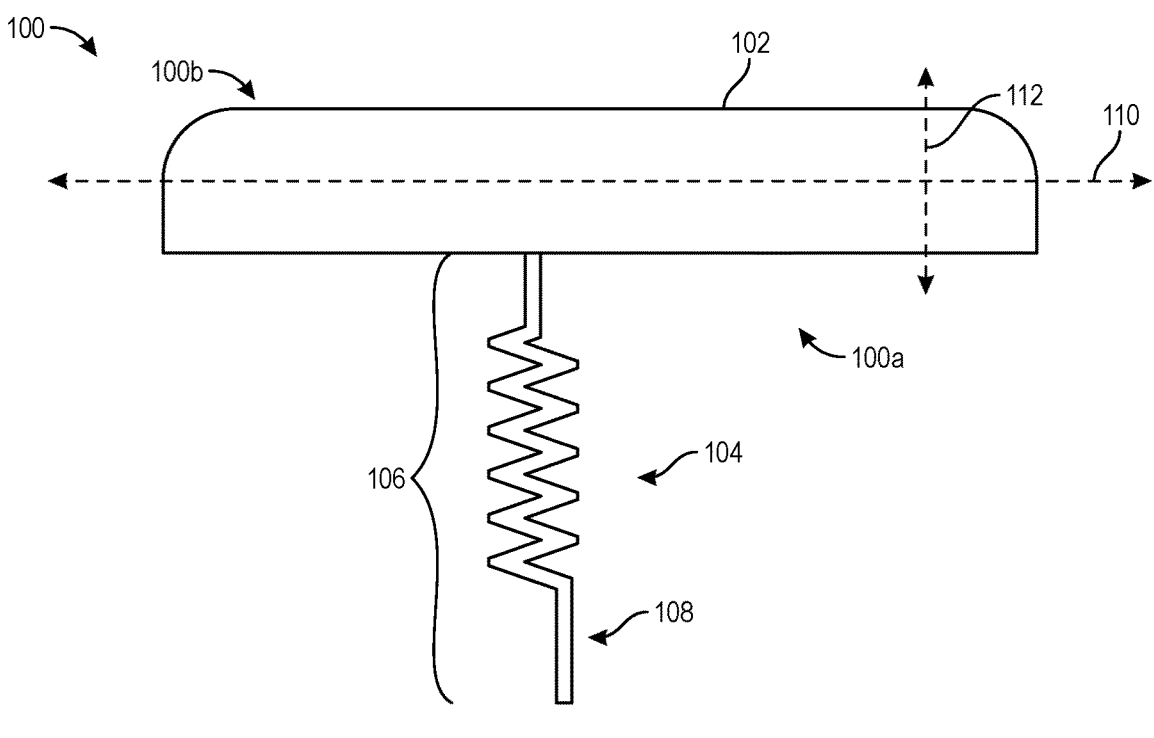
FIG. 1 is a side view of a sensor assembly configured in accordance with several embodiments of the present technology.

Embodiments of the present disclosure generally relate to wearable sensors for monitoring analyte levels in vivo and applicators for inserting at least a portion of a wearable sensor in a patient's body. In various embodiments, an analyte may refer to, without limitation, a substance or chemical constituent in a biological fluid (e.g., blood, interstitial fluid, cerebral spinal fluid, lymph fluid or urine) that can be analyzed. While non-limiting embodiments are described below that relate to continuous glucose sensing for treating diabetes, it should be appreciated that the present technology is not limited for use with glucose sensors or to treating diabetes and can be configured for use with any one of a variety of sensors known in the art to treat a range of medical conditions.

Existing blood glucose (BG) sensors typically comprise a base portion configured to reside on the patient's skin and a sensor portion extending away from the base portion and configured to be inserted subcutaneously in the patient's body. To facilitate insertion of the sensor portion, the sensor is typically loaded in an insertion tool with the sensor portion disposed within a needle of the insertion tool. The needle is carried by an insertion mechanism that, when activated by a user, drives the needle into the patient's skin and simultaneously inserts the sensor portion. The insertion tool and needle are then withdrawn, leaving behind the base portion and inserted sensor portion.

Existing sensor insertion tools can be large and bulky, making it burdensome for a user to carry the insertion tools on their person and generating large amounts of disposal waste. The bulkiness of conventional inserters is in large part due to the arrangement of the sensor assembly and needle insertion components within the housing of the inserter. Several prior art devices comprise insertion tools, for example, in which the base portion of the sensory assembly is loaded directly below the needle carrier and in the path of needle insertion. As such, the base portion has an opening extending through its entire thickness and through which the needle moves during insertion and retraction. Having such an opening in the base portion is less than optimal, as the opening occupies valuable space that could otherwise be used for electronics or other sensor components, or eliminated altogether to enable a smaller base portion. These and other drawbacks are discussed in greater detail below.

The sensor assemblies and associated applicators described herein can overcome the foregoing issues with prior art devices. For example, the present technology includes an applicator assembly in which the sensor assembly and needle carrier are arranged side-by-side, rather than stacked vertically. The resulting applicator is significantly slimmer than prior art assemblies and eliminates the need for a needle opening in the base portion, thus also enabling smaller sensor bases. According to some embodiments, the present technology includes a sensor applicator comprising a housing having an insertion end configured to be positioned at or adjacent a user's skin at an insertion site, a needle carried by the housing and configured for insertion into the user's skin at the insertion site, and a sensor assembly comprising a base and a sensing portion coupled to the base. The base is supported by the housing in a first position during insertion of the needle and configured to rotate into a second, laid-flat position on the user's skin after removal of the housing from the insertion site.

FIG. 1 shows a sensor assembly 100 for monitoring analyte levels in vivo in accordance with several embodiments of the present technology. The sensor assembly 100 can comprise a base 102 configured to reside on a user's skin and a sensor 104 coupled to and extending away from the base 102. The base 102 has a bottom side 100a configured to be secured to a user's skin and a top side 100b. The sensor 104 can comprise an extension 106 extending distally away from the bottom side 100a of the base 102 and a sensing portion 108 at a distal portion of the extension 106 that is configured to be implanted in a user's skin. The extension 106 provides a flexible electrical connection between the sensing portion 108 and the base 102. In some embodiments, the sensing portion 108 is an electrochemical sensor that includes a glucose oxidase enzyme that enables the sensing portion 108 to monitor blood glucose levels in a diabetic patient by effecting a reaction of glucose and oxygen. In other embodiments, the sensing portion 108 comprises other electrochemical sensors.

All or a portion of the extension 106 can be configured to flex, bend, fold, coil, collapse, extend and/or otherwise be manipulated to accommodate movement of the sensing portion 108 towards and/or away from the base 102. In some embodiments, the extension 106 can comprise electronic components mounted on a flexible substrate. The extension 106 can comprise, for example, a flexible circuit such as a flat flex circuit or a flexible cable. In some embodiments, all or a portion of the extension 106 has an accordion or coil structure extendable away from the base 102 and retractable inwardly toward the base 102.

Figure 2:
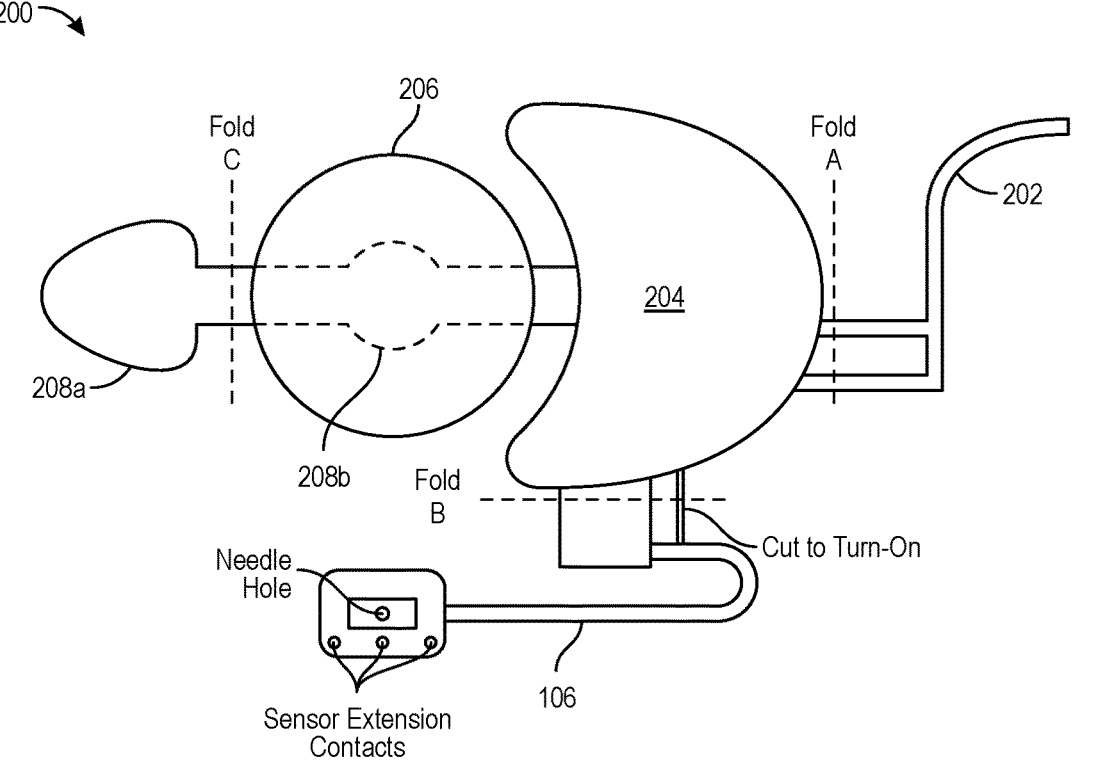
FIG. 2 is a schematic diagram showing example electronics component for use with the sensor assemblies of the present technology.

The base 102 is configured to provide structural support to the extension 106 and/or sensing portion 108 while the sensing portion 108 is implanted subcutaneously. As shown in FIG. 1, the base 102 can have a long dimension 110 and a short dimension 112. The long dimension 110, for example, can extend between the sides of the base 102, and the short dimension 112 can extend between a top and bottom surface of the base 102. The base 102 can comprise any suitable shape, including a circle, a square, an oval, a rectangle, a triangle, or others. Unlike some existing sensors, the base 102 does not have any openings extending through its thickness. The base 102 may further include one or more electronic components, such as a wireless transmitter that communicates with an infusion pump, monitor device, or the like. As shown in the schematic diagram 200 of FIG. 2, in some embodiments the base 102 includes an antenna 202, a printed circuit board assembly 204 (hereafter PCBA 204), and a battery 206 having battery contacts 208*a*, 208*b*. The electronic components can be configured to fold on top of one another for a more compact arrangement. For example, the antenna 202 can be configured to fold over line A above the PCBA 204 and the extension 106 can be configured to fold over line B beneath the PCBA 204. One of the battery contacts (208*b*) can be under the battery 206, and the other battery contact 208*a* can be configured to fold over line C onto the top of and/or in electrical communication with the battery. In other embodiments the contact points on the battery 206 can be in different positions. Advantageously, the components can be compressed or otherwise fit together such that no solder or other connections are necessary for the sensor assembly 100. In this way, the arrangement minimizes dead volume and reduces the thickness of the sensor assembly 100.

In some embodiments, some or all of the electronic components can be provided in a separate unit (or multiple units) that is configured to be detachably coupled to the base 102 and/or associated applicator. The separate electronics component can be re-usable while the sensor assembly 100 remains configured for single-use. Alternatively, the sensor assembly 100 and the electronic components can be packaged and shipped together.

Portions of the sensor assembly 100 are formed at least in part of a plastic material. In various embodiments, the bulk of the sensor assembly 100 is formed as molded plastic components. In other embodiments, the sensor assembly 100 is formed from ABS, nylon, an ABS/PC blend, PVC, polytetrafluoroethylene (PTFE), polypropylene, polyether ether ketone (PEEK), polycarbonate, or the like.

Figure 3:
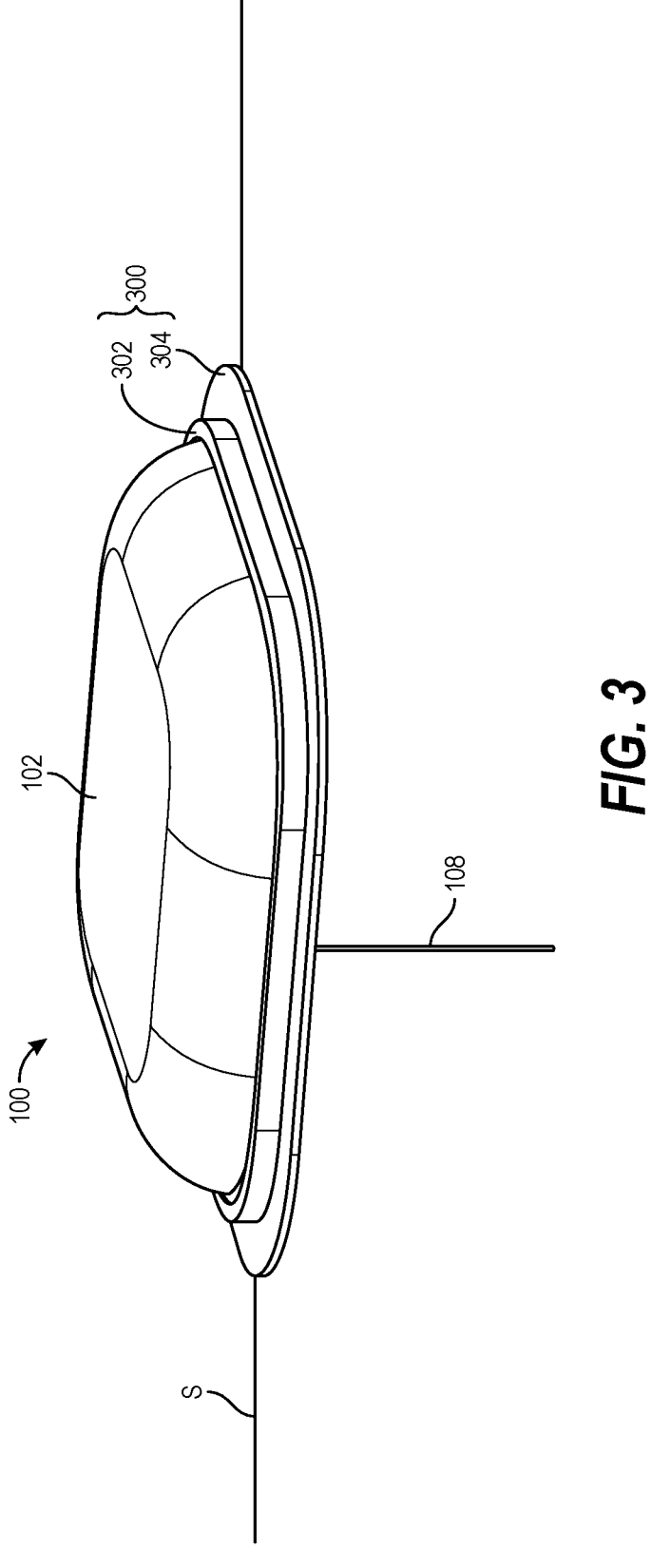
FIG. 3 is a perspective view of a sensor assembly configured in accordance with several embodiments of the present technology, shown positioned on a patient's skin.

In some embodiments, the sensor assembly 100 can be configured to sit on and/or within a support that affixes the sensor assembly 100 to the skin of the patient. FIG. 3, for example, shows the sensor assembly 100 positioned on a support 300 that is adhered to a user's skin S. The support

300 can have a top surface 304 that attaches to at least a portion of a bottom surface of the base 102, and a bottom surface (not visible) that is configured to be attached to the skin of the user also using an adhesive (e.g., a fluid adhesive, a spray adhesive, etc.). The attachment between the support 300 and the bottom surface of the base 102 can be an adhesive attachment, a snap fit attachment, and/or other suitable attachment means. In some embodiments, the support 300 includes a rail 302 that extends upwardly from the top surface 304 and around a perimeter of the base 102. The rail 302 can bound an area substantially equivalent to a footprint of the base 102 such that, when positioned on the support 300 within the railed area, the base 102 is prevented from sliding and/or rotating relative to the support 300. In one or more embodiments, the support 300 comprises a flexible and breathable material with adhesive properties, such as cloth, a bandage-like material, and the like. Suitable materials include, for example, polyurethane, polyethylene, polyester, polypropylene, polytetrafluoroethylene (PTFE), or other polymers. In other embodiments, the support 300 is made of solid materials, for example, plastic, etc.

Figure 4B:
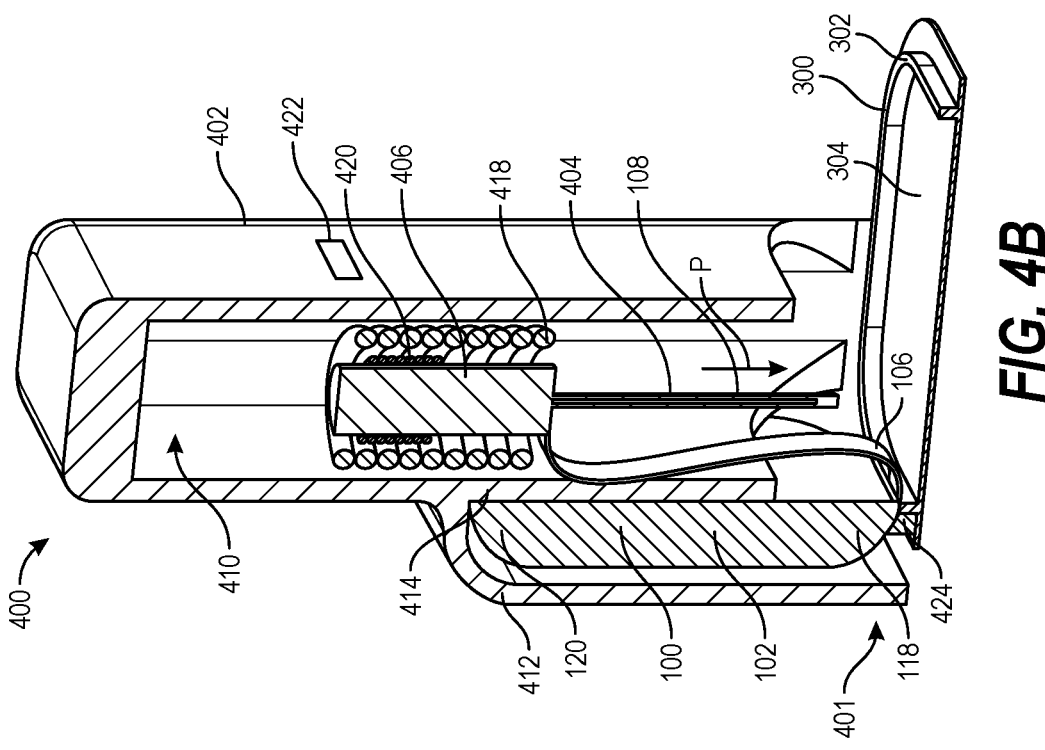
FIG. 4B shows the applicator assembly of FIG. 4A with a portion of the housing and some of the contents removed for ease of viewing certain components.
Figure 4A:
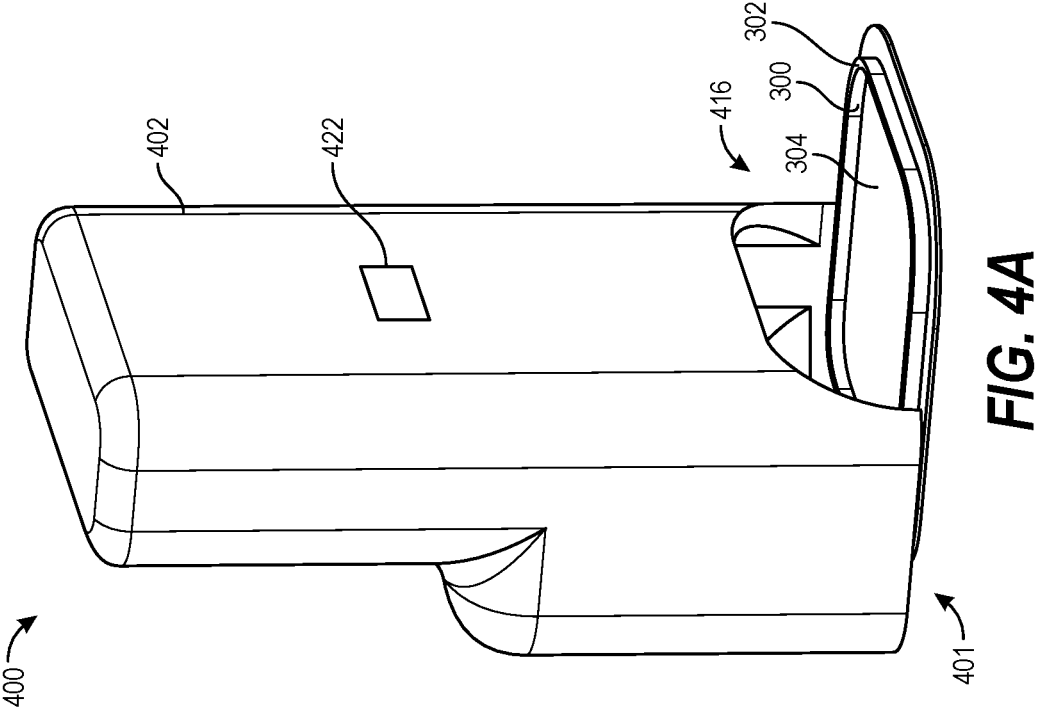
FIG. 4A is a perspective view of an applicator assembly configured in accordance with several embodiments of the present technology.

FIG. 4A is a perspective outer view of an applicator assembly 400 (or "applicator 400") configured for use with the sensor assembly 100 of the present technology. FIG. 4B is a cutaway view of the applicator 400 showing only select internal components. In FIGS. 4A and 4B, the applicator 400 is shown in a pre-insertion state. The applicator 400 includes a housing 402 defining an interior cavity and having an insertion end 401 configured to be positioned on or adjacent a patient's skin at an insertion site. In some embodiments, the insertion end 401 of the housing 402 is configured to be positioned on and/or received by a support 300 adhered to the user's skin at the insertion site. The rail 302 and/or top surface 304 of the support 300 can engage the insertion end 401 of the housing 402 to stabilize the applicator 400 during use. In some embodiments, the insertion end 401 of the housing 402 is configured to be positioned directly against the skin and/or the applicator 400 includes an integrated mounting base and/or support at or near the insertion end 401. As shown in FIG. 4A, in some embodiments the housing 402 can have a cut-out and/or opening 416 in the sidewall near the insertion end 401 that enables folding of the support 300 when stored. In certain embodiments, the support 300 does not include the rail 302 and instead comprises a flat adhesive surface.

The applicator 400 can include a needle 404 and a needle carrier 406 positioned within the cavity of the housing 402. The applicator 400 is also configured to receive and support the sensor assembly 100, which may come pre-loaded within the applicator 400, or the sensor assembly 100 may be packaged separately and can be loaded by the user into the applicator 400. Either way, once mounted within the housing 402 and/or otherwise secured to the housing 402, the base 102 of the sensor assembly 100 can be coupled to the needle 404 via the sensing portion 108 that can extend around or through a portion of the needle 404. As a result, deployment of the needle 404 by the user guides the sensing portion 108 of the sensor assembly 100 into the patient's body.

Figure 4D:
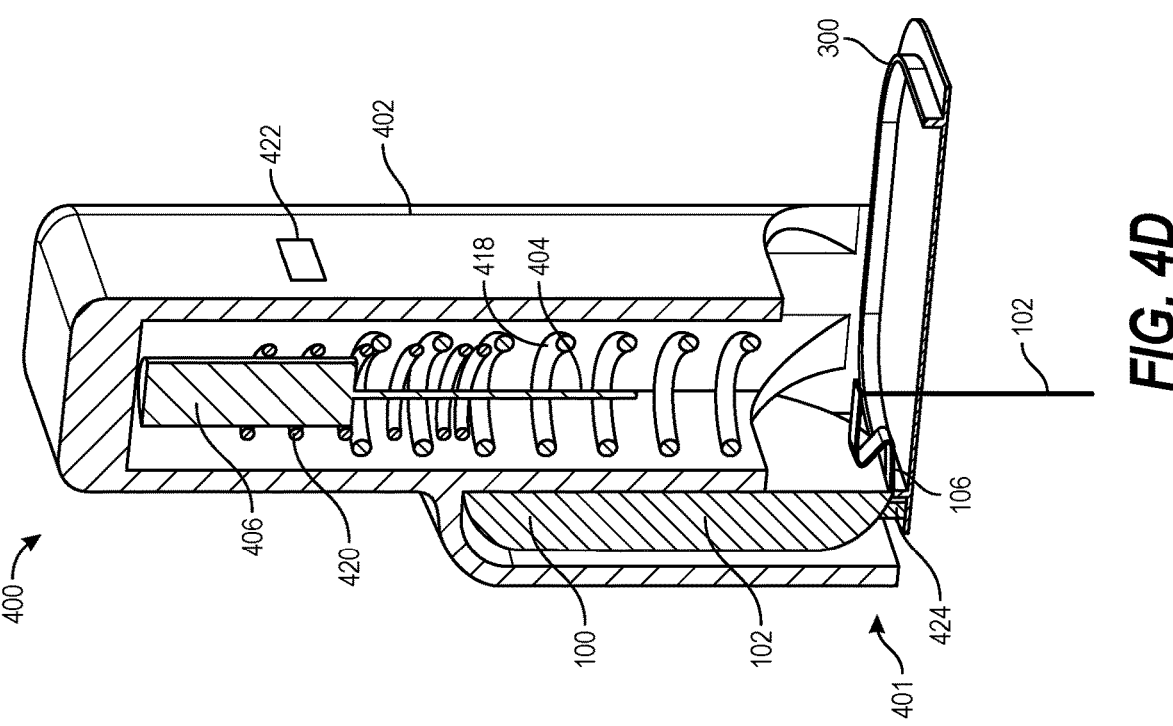
FIG. 4D shows the applicator assembly of FIG. 4B in a retracted state in accordance with several embodiments of the present technology.
Figure 4C:
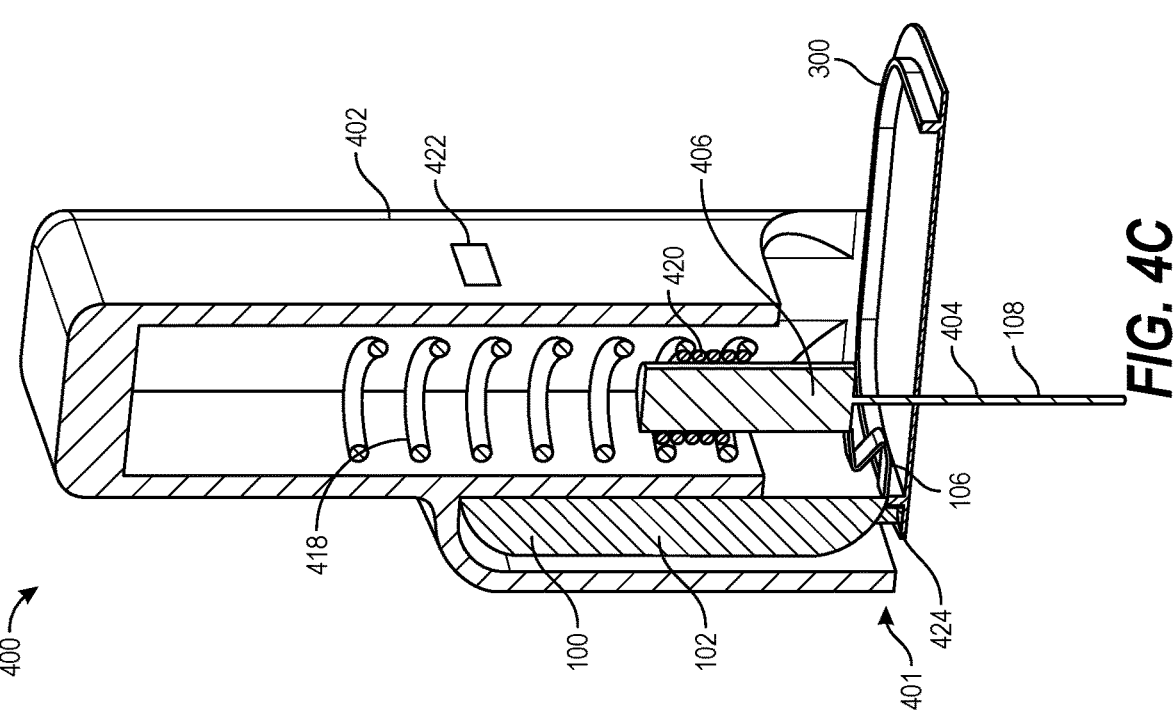
FIG. 4C illustrates the applicator assembly of FIG. 4B in an insertion state in accordance with several embodiments of the present technology.

While not shown in full in FIG. 4B, the applicator 400 can include an insertion assembly coupled to the needle 404 and/or needle carrier 406 and configured to move the needle 404 from a pre-insertion position within the housing 402 to an extended position in which a distal end of the needle 404 projects relative to the housing 402 (see FIG. 4C). The insertion assembly can include, for example, a first spring 418 positioned between a portion of the needle carrier 406 and the housing 402 (or component therein) and held in compression when the applicator is in a pre-insertion state. When insertion is desired, a user may cause the first spring 418 to be released (e.g., via activation of the trigger 422), thereby pushing the needle carrier 406 downwardly towards the insertion end 401 of the housing 402 and into the user's skin. In some embodiments, the applicator 400 further includes a retraction assembly (not fully shown) coupled to the needle 404 and/or needle carrier 406 that is configured to move the needle 404 from the extended position to a retracted position in which the distal end of the needle 404 is within the housing 402. The retraction assembly can include, for example, a second spring 420 positioned between a portion of the needle carrier 406 and the housing 402 (or component therein) and held in compression until the needle 404 reaches the extended position. Once released, the second spring 420 pushes the needle 404 and/or needle carrier 406 upwardly (as shown in FIG. 4D) until the sharp distal end of the needle 404 is contained and protected by the housing 402. The first and second springs 418, 420 are not shown in FIGS. 4E and 4F for ease of illustration. In any of the embodiments disclosed herein, the needle carrier 406 can include one or more slots, grooves, shelves, and/or protrusions that guide the movement of the needle carrier 406 when in motion, as well as guide and retain the first and second springs 418, 420.

As best shown in FIG. 4B, the applicator 400 is configured to receive and support the sensor assembly 100. The applicator 400 may be shipped with the sensor assembly 100 pre-loaded therein, or the sensor assembly 100 may be packaged separately and can be loaded by the user into the applicator 400. For example, in some embodiments the applicator 400 is configured for use with both re-usable and disposable components, as discussed in greater detail herein. In any case, the housing 402 of the applicator 400 can be configured to support the base 102 of the sensor assembly 100 in an "upright position" during insertion of the needle 404. In this upright position, the base 102 is rotated about 90 degrees relative to its intended "laid-flat position" when residing on the user's skin during use. For example, the base 102 can be supported by the housing 402 in a first orientation in which the first end 118 of the base 102 is adjacent the user's skin and the second end 120 is spaced apart from the user's skin by a distance equivalent to a length of the long dimension 110 (see FIG. 1) of the base 102. As such, when the insertion end 401 of the applicator 400 is positioned at or adjacent the user's skin at an insertion site, the short dimension 112 (see FIG. 1) of the base 102 is substantially parallel to the skin and the long dimension 110 (see FIG. 1) of the base 102 is substantially parallel to the insertion path P of the needle 404. As discussed in greater detail below, after insertion of the needle 404 and removal of the applicator 400 from the insertion site, the base 102 rotates downwardly into a laid-flat position on the skin. Advantageously, only having to move the sensor 104 vertically and the upright orientation of the base 102 in the applicator 400 enables the applicator 400 to have a thin profile, unlike existing insertion devices that are built around moving an entire sensor assembly in a laid-flat orientation. The applicators of the present technology are thus much easier for the user to carry on their person (for example, in a purse or pocket) and create less waste. The smaller applicators can also be shipped, stored, and sterilized in greater volumes.

Referring still to FIG. 4B, the base 102 can be positioned within the housing 402 laterally adjacent the needle 404 and/or needle carrier 406 such that the entire base 102 is clear of the needle insertion path P. In some embodiments, for example, the housing 402 can comprise a first compartment 410 configured to house the needle 404, needle carrier 406, insertion assembly, and/or retraction assembly and a second compartment 412 configured to house the base 102 in an upright position. The first and second compartments 410, 412 can be separated by a wall 414. As previously mentioned, several existing insertion devices position the sensor base in the insertion path of the needle, thereby requiring the sensor base to have an opening through which the needle can pass. Because of the side-by-side arrangement of the base 102 and needle 404 of the present technology, the base 102 does not require a needle opening and thus eliminates the components required to seal the opening (such as one or more o-rings). Removal of the needle hole in the base also enables the base portion to be smaller (as it no longer has to accommodate the opening) and increases the amount of surface area available on the PCBA, antenna, and/or other electronic components. Elimination of the needle hole also enables e-beam sterilization of the applicator 400, which has many benefits over EtO sterilization and allows for low-cost turn on methods. Sterilization using the traditional EtO method uses environmentally toxic chemicals and, in the future, may be banned. Using e-beam can damage the electronics, however, so moving the sensor and needle assembly away from one another (using the flexible extension 106, for example) enables the e-beam to be directed at only the necessary areas of the system (such as the needle).

Even though the base 102 is mechanically linked to the needle 404 via the sensing portion 108 (at least until retraction of the needle 404), the flexible extension 106 effectively decouples movement of the needle 404 and/or needle carrier 406 from the base 102. As such, the sensing portion 108 of the extension 106 can move downwardly with the needle 404 during insertion without causing movement of the base 102. This decoupling of the base 102 and the needle 404 provides several benefits over existing insertion devices in which the base 102 is coupled to and moves with the needle 404 and/or needle carrier 406. Because the insertion assembly no longer has to push the base 102 in addition to the needle 404 during insertion, the insertion force required to insert the needle 404 is less, thereby reducing the impact force on the user and enabling the use of a smaller insertion spring. Removal of the base 102 from the insertion assembly also enables a lower-cost analyte monitoring system that utilizes both re-usable and disposable components, for example as described with reference to FIG. 8 below.

FIG. 4C illustrates the applicator 400 in an insertion state in accordance with several embodiments of the present technology. In the insertion state, the needle 404 and needle carrier 406 are in an extended position in which the distal end of the needle 404 projects from the housing 402, through the support 300 and into a user's skin. A user may activate insertion of the needle 404 via a trigger 422 disposed on the housing 402, a remote trigger, or other methods. As the first spring 418 causes the needle 404 to move downwardly toward the insertion site, the needle 404 brings the sensing portion 108 of the sensor 104 with it, thereby decreasing a distance between a proximal end of the extension 106 and the sensing portion 108. In response to this movement, the flexible extension 106 can be configured to bend, fold, and/or coil along its longitudinal axis to accommodate the compression in the extension 106. As shown in FIG. 4C, in some embodiments the extension 106 can accommodate such compression by folding along its longitudinal axis, similar to an accordion.

FIG. 4D shows the applicator 400 in a post-insertion state with the needle 404 in a retracted position. In some embodiments, insertion of the needle 404 can trigger the retraction assembly, such as the second spring 420, to retract the needle 404 into the housing, thereby leaving the sensing portion 108 behind in the user's body.

Figure 4F:
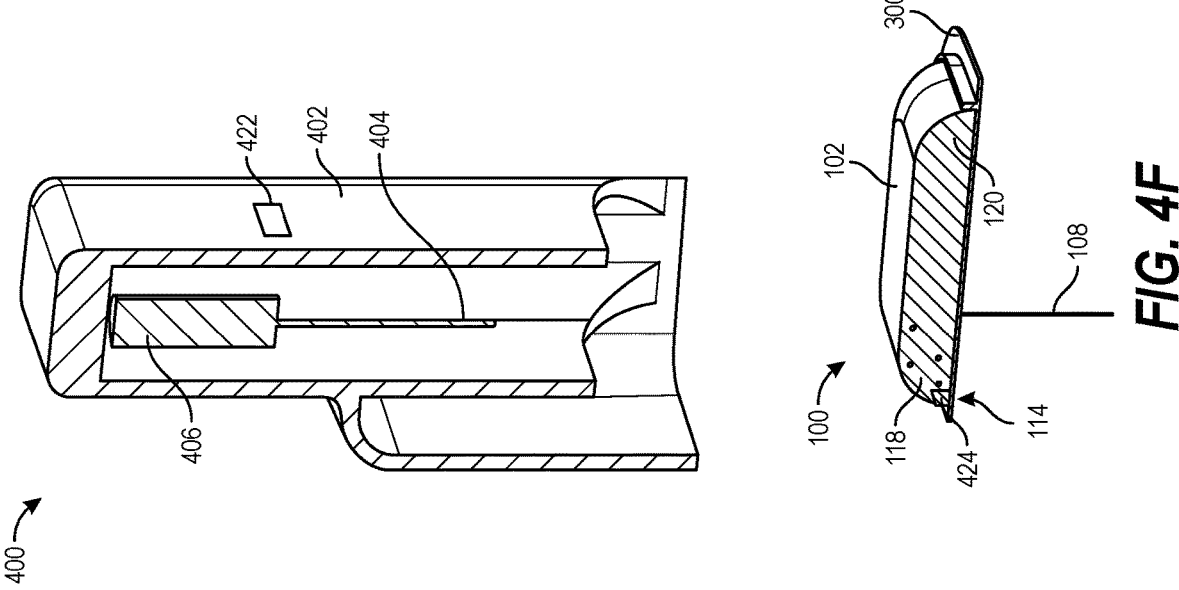
FIG. 4F shows an insertion site after the applicator assembly of FIG. 4B has been removed, leaving the sensor assembly behind in a laid-flat position.
Figure 4E:
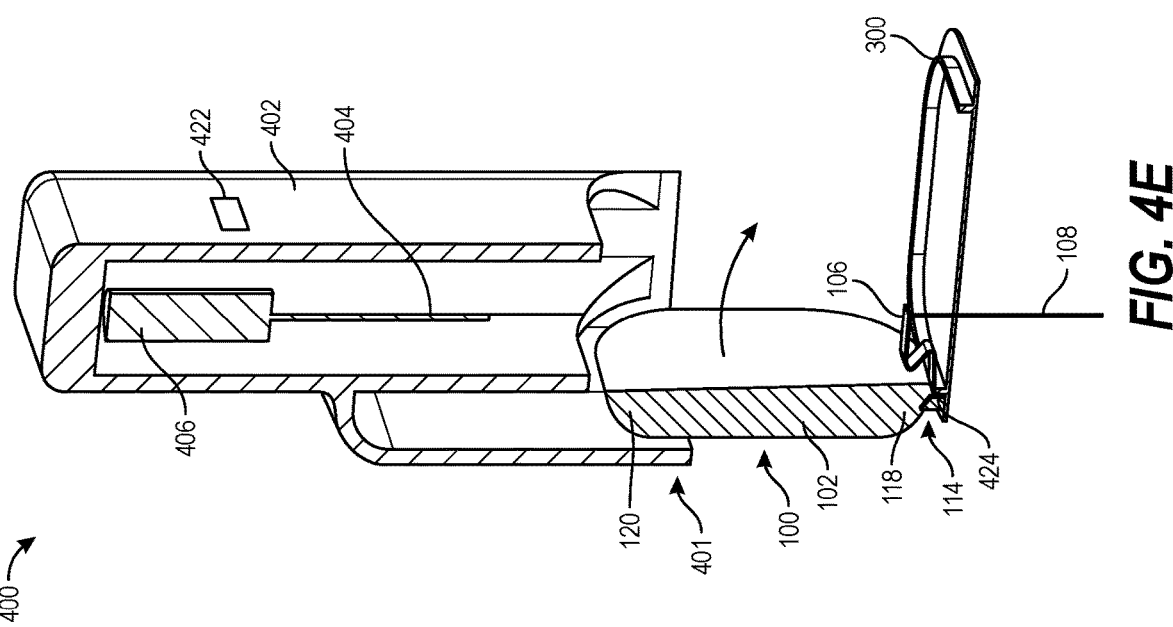
FIG. 4E shows the applicator assembly of FIG. 4B as the applicator assembly is being withdrawn from the insertion site, while the sensor assembly is in an insertion position.

As shown in FIG. 4E, the applicator housing 402 can then be withdrawn from the insertion site, thereby exposing the base 102 in the upright position. As shown in FIG. 4F, the base 102 is configured to rotate downwardly towards the skin and/or support 300 until the base 102 is engaged with the support 300 and positioned on the skin in a laid-flat position. In this orientation, both the first and second ends 118, 120 of the base 102 are adjacent the user's skin.

In some embodiments, the base 102 is configured to rotate about its end 114 that is closest to the skin and/or support 300. The base 102 can be configured to rotate at least 45 degrees, at least 60 degrees, or at least 90 degrees between the upright position and the laid-flat position. In some embodiments, the base 102 is configured to automatically rotate downwardly, towards the laid-flat position, upon removal of the housing 402. For example, the base 102 may comprise a spring-loaded hinge at its pivot end 114. In these and other embodiments, the base 102 comprises a living hinge at its pivot end 114. Alternatively, the base 102 may be configured for manual rotation by a user from the upright position to a laid-flat position.

In some embodiments, the base 102 is coupled to the support 300 by a bending portion and/or joint (both represented schematically in FIG. 4E as element 424). The bending portion and/or joint can be a torsion spring, a hinge, a flap, a plastic spring, and/or other means for coupling the base 102 to the support 300 and causing or allowing the base 102 to rotate downwardly onto the support 300.

As the base 102 rotates downwardly, a bottom surface of the base 102 is positioned on top of and/or covers the compressed extension 106. In some embodiments, the base 102 includes a recessed portion (not shown) at its bottom surface that is configured to receive the extension 106 therein and accommodate the extra thickness generated by the compressed extension 106 so that the compressed extension 106 does not increase a thickness of the base 102.

Figure 5A:
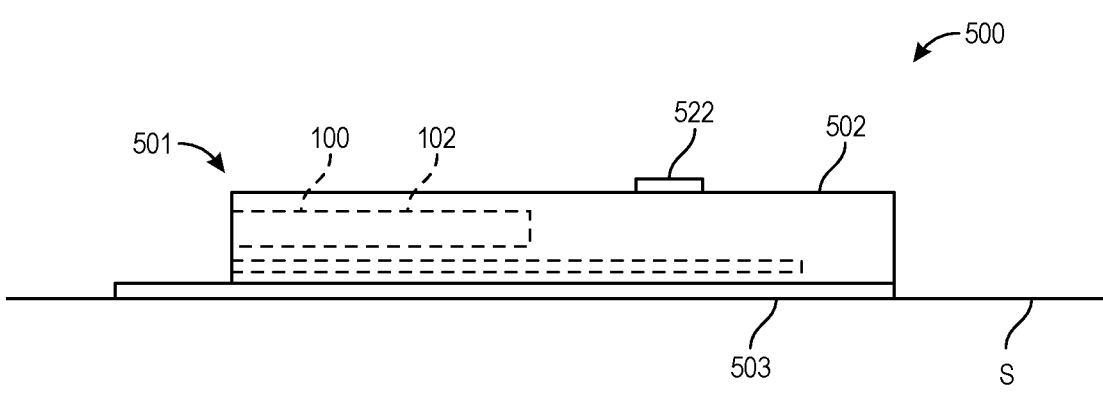
FIG. 5A shows an applicator assembly configured in accordance with several embodiments of the present technology, shown adhered in a first pre-insertion state to a user's skin.

FIG. 5A schematically depicts an applicator assembly 500 (or "applicator 500") configured in accordance with several embodiments of the present technology, shown adhered in a first pre-insertion state to a user's skin S. Unlike the applicator 400 depicted in FIGS. 4A-4F, the applicator 500 is initially placed flat on the user's skin S in a horizontal orientation Similar to applicator 400, the applicator 500 includes a housing 502 defining an interior cavity and having an insertion end 501 configured to be positioned on or adjacent a patient's skin at an insertion site. In some embodiments, the insertion end 501 of the housing 502 is configured to be positioned on and/or received by a support 503 adhered to the user's skin at the insertion site. The support 503 used for stabilizing the applicator 500 can be larger and/or include a stronger adhesive than the support 300 used with the applicator 400, as the applicator 500 requires an additional motion (detailed below) to prepare the applicator 500 for insertion.

The applicator 500 can include a needle 504 and a needle carrier (not depicted) positioned within the housing 502. In some embodiments, the needle carrier can be structurally similar to the needle carrier 406 described above with reference to FIGS. 4B-4F. The applicator 500 is also configured to receive and support the sensor assembly 100, which may come pre-loaded within the applicator 500, or the sensor assembly 100 may be packaged separately and can be loaded by the user into the applicator 500. Either way, once mounted within the housing 502 and/or otherwise secured to the housing 502, the base 102 of the sensor assembly 100 can be coupled to the needle 504 via the sensing portion 108 that can extend around or through a portion of the needle 504. As a result, deployment of the needle 504 by the user guides the sensing portion 108 of the sensor assembly 100 into the patient's body.

Figure 5B:
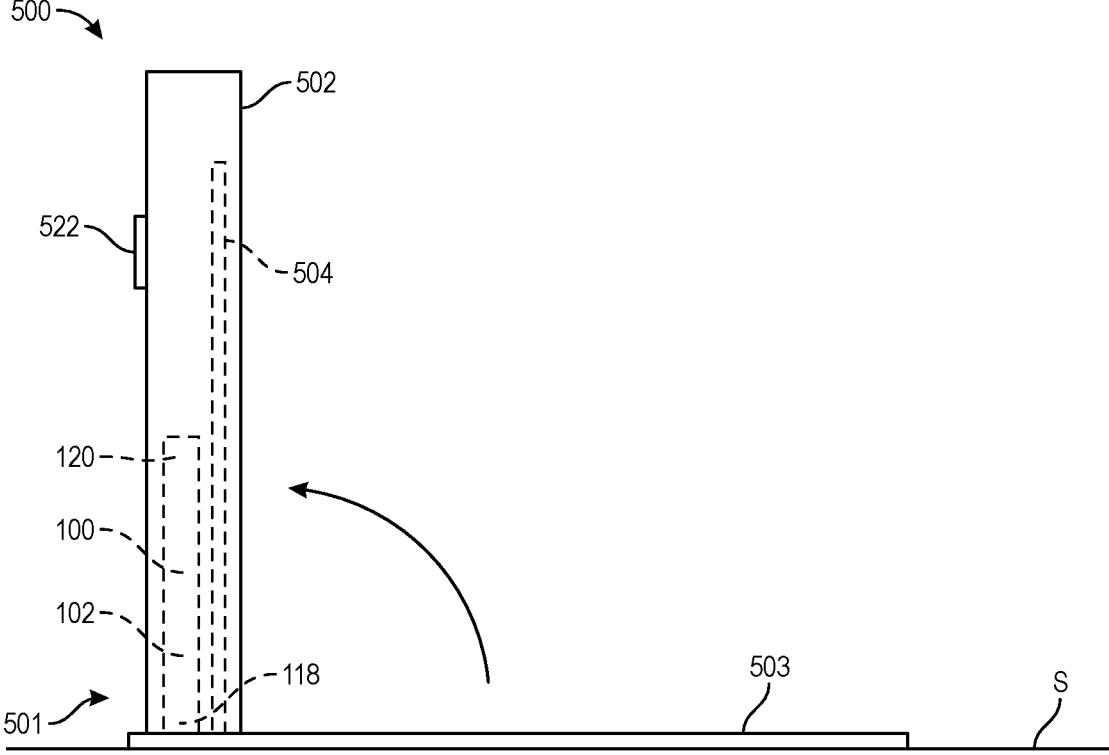
FIG. 5B shows the applicator assembly of FIG. 5A in a second pre-insertion state in accordance with several embodiments of the present technology.

To prepare the needle 504 for insertion, the applicator 500 can be rotated upwardly until the needle 504 is substantially perpendicular to the skin S. FIG. 5B, for example, shows the applicator 500 in this second pre-insertion state. While not shown in FIG. 5B, the applicator 500 can include an insertion assembly (similar to the insertion assembly described above in connection with FIGS. 4A-4F) coupled to the needle 504 and/or needle carrier and configured to move the needle 504 from a pre-insertion position within the housing 502 to an extended position in which a distal end of the needle 504 projects relative to the insertion end of the housing 502 (see FIG. 5C). The insertion assembly can include, for example, a first spring positioned between a portion of the needle carrier and the housing 502 (or component therein) and held in compression when the applicator 500 is in a pre-insertion state. When insertion is desired, a user may cause the first spring to be released, thereby pushing the needle carrier downwardly towards the insertion end of the housing 502 and into the user's skin. In some embodiments, the applicator 500 further includes a retraction assembly (not shown) coupled to the needle 504 and/or needle carrier that is configured to move the needle 504 from the extended position to a retracted position in which the distal end of the needle 504 is within the housing 502. The retraction assembly can include, for example, a second spring positioned between a portion of the needle carrier 506 and the housing 502 (or component therein) and held in compression until the needle 504 reaches the extended position. Once released, the second spring pushes the needle 504 and/or needle carrier upwardly until the sharp distal end of the needle 504 contained and protected by the housing 502.

Similar to applicator 400, the applicator 500 is configured to receive and support the sensor assembly 100. The applicator 500 may be shipped with the sensor assembly 100 pre-loaded therein, or the sensor assembly 100 may be packaged separately and can be loaded by the user into the applicator 500. For example, in some embodiments the applicator 500 is configured for use with both re-usable and disposable components, as discussed in greater detail herein. In any case, the housing 502 can be configured to support the base 102 of the sensor assembly 100 in an "upright position" during insertion of the needle 504. In this upright position, the base 102 is rotated about 90 degrees relative to its intended "laid-flat position" when residing on the user's skin during use. For example, the base 102 can be supported by the housing 502 in a first orientation in which the first end 118 of the base 102 is adjacent the user's skin and the second end 120 is spaced apart from the user's skin by a distance equivalent to a length of the long dimension 110 (see FIG. 1) of the base 102. As such, when the insertion end of the applicator 500 is positioned at or adjacent the user's skin at an insertion site, the short dimension 112 (see FIG. 1) of the base 102 is substantially parallel to the skin and the long dimension 110 (see FIG. 1) of the base 102 is substantially parallel to the insertion path P of the needle 404. As discussed in greater detail below, after insertion of the needle 504 and removal of the applicator 500 from the insertion site, the base 102 rotates downwardly into a laid-flat position on the skin. Advantageously, the upright orientation of the base 102 in the applicator 500 enables the applicator 500 to have a thin profile, which provides several benefits over the prior as detailed above.

Referring still to FIG. 5B, the base 102 can be positioned within the housing 502 laterally adjacent the needle 504 and/or needle carrier such that the entire base 102 is clear of the needle insertion path. As previously mentioned, several existing insertion devices position the sensor base in the insertion path of the needle, thereby requiring the sensor base to have an opening through which the needle can pass. The side-by-side arrangement of the base 102 and needle 504 provide numerous advantages as detailed herein.

Even though the base 102 is mechanically linked to the needle 504 via the sensing portion 108 (at least until retraction of the needle 504), the flexible extension 106 effectively decouples movement of the needle 504 and/or needle carrier from the base 102. As such, the sensing portion 108 can move downwardly with the needle 504 during insertion without causing movement of the base 102. This decoupling of the base 102 and the needle 504 provides several benefits over existing insertion devices in which the base 102 is coupled to and moves with the needle 504 and/or needle carrier. Because the insertion assembly no longer has to push the base 102 in addition to the needle 504 during insertion, the insertion force required to insert the needle 504 is less, thereby reducing the impact force on the user and enabling the user of a smaller insertion spring.

Removal of the base 102 from the insertion assembly also enables a lower-cost analyte monitoring system that utilizes both re-usable and disposable components, as detailed herein.

Figure 5C:
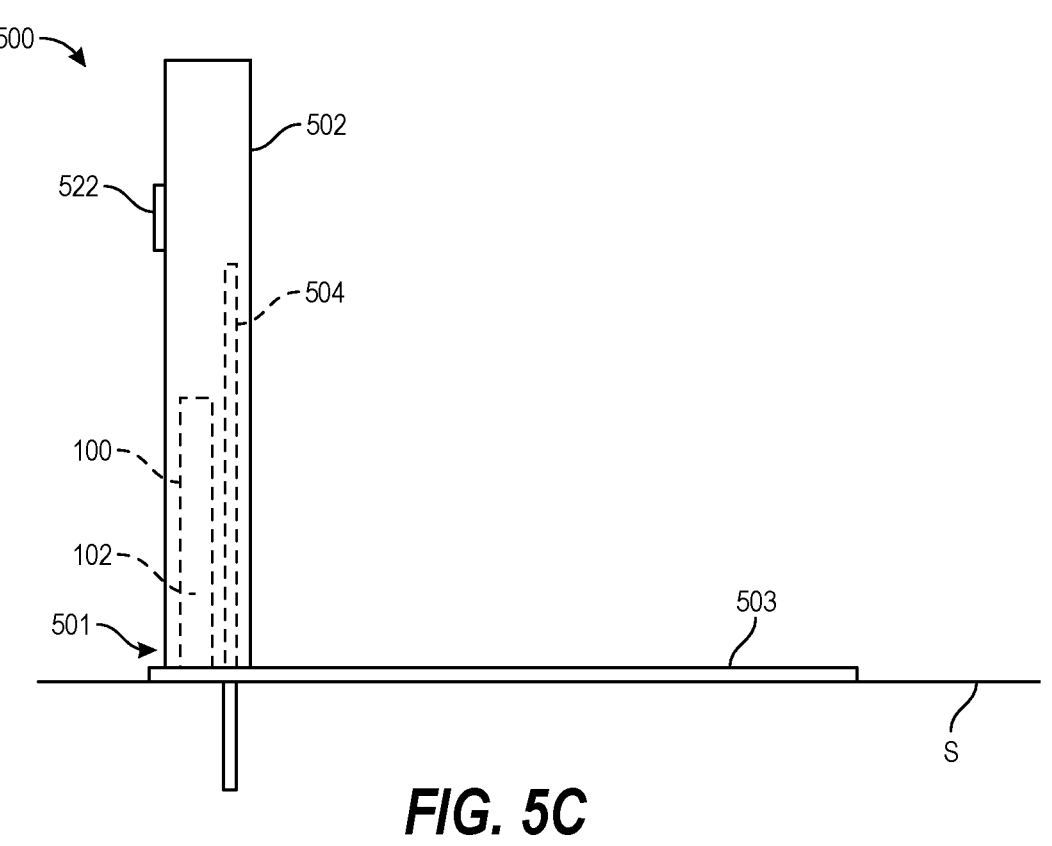
FIG. 5C shows the applicator assembly of FIG. 5A in an insertion state in accordance with several embodiments of the present technology.
Figure 5D:
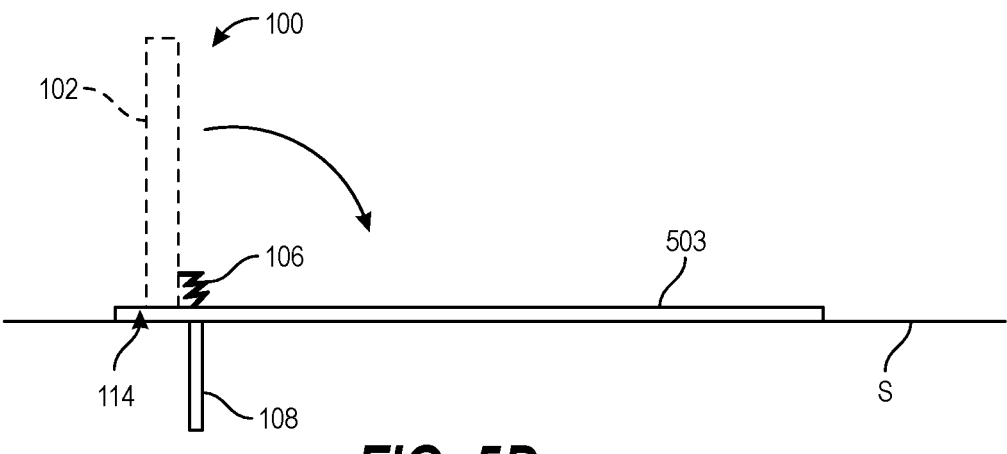
FIG. 5D shows an insertion site after the applicator assembly of FIG. 5A has been removed, with a base of the sensor assembly exposed.

FIG. 5C shows the applicator assembly 500 in an insertion state in accordance with several embodiments of the present technology. In the insertion state, the needle 504 and needle carrier are in an extended position in which the distal end of the needle 504 projects from the housing 502, through the support 503 and into a user's skin. A user may activate insertion of the needle 504 via a trigger 522 disposed on the housing 502, a remote trigger, or other methods. As the needle 504 moves downwardly toward the insertion site, the needle 504 brings the sensing portion (not visible) with it, thereby decreasing a distance between a proximal end of the sensing portion and a distal end of the sensing portion. In response to this movement, the flexible extension can be configured to bend, fold, and/or coil along its longitudinal axis to accommodate the compression in the sensing portion. As best shown in FIG. 5D, in some embodiments the extension 106 can accommodate such compression by folding along its longitudinal axis, similar to an accordion. Insertion of the needle 504 can trigger the retraction assembly to retract the needle 504 into the housing, thereby leaving the sensing portion 108 behind in the user's body.

Figure 5E:
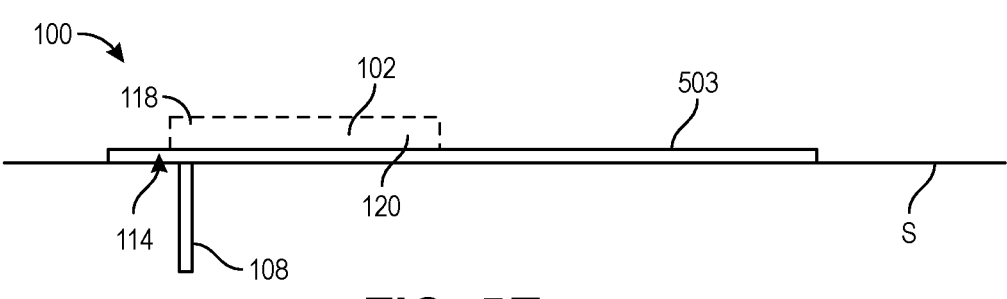
FIG. 5E shows the insertion site of FIG. 5D after the sensor assembly has been rotated into a monitoring position.

FIG. 5D shows the insertion site after the applicator 500 has been removed, leaving the sensor assembly 100 with the sensing portion 108 inserted in the body and exposing the base 102 in the upright position. As shown in FIG. 5E, the base 102 is configured to rotate downwardly towards the skin and/or support 503 until the base 102 is positioned on the skin in a laid-flat position. In this orientation, both the first and second ends 118, 120 of the base 102 are adjacent the user's skin.

In some embodiments, the base 102 is configured to rotate about its end 114 that is closest to the skin and/or support 503. The base 102 can be configured to rotate at least 45 degrees, at least 60 degrees, or at least 90 degrees between the upright position and the laid-flat position. In some embodiments, the base 102 is configured to automatically rotate downwardly, towards the laid-flat position, upon removal of the housing 502. For example, the base 102 may comprise a spring-loaded hinge at its pivot end 114. In these and other embodiments, the base 102 comprises a living hinge at its pivot end 114. Alternatively, the base 102 may be configured for manual rotation by a user from the upright position to a laid-flat position.

As the base 102 rotates downwardly, a bottom surface of the base 102 is positioned on top of and/or covers the compressed extension 106. In some embodiments, the base 102 includes a recessed portion (not shown) at its bottom surface that is configured to receive the extension 106 therein and accommodate the extra thickness generated by the compressed extension 106 so that the compressed extension 106 does not increase a thickness of the base 102.

Figure 6A:
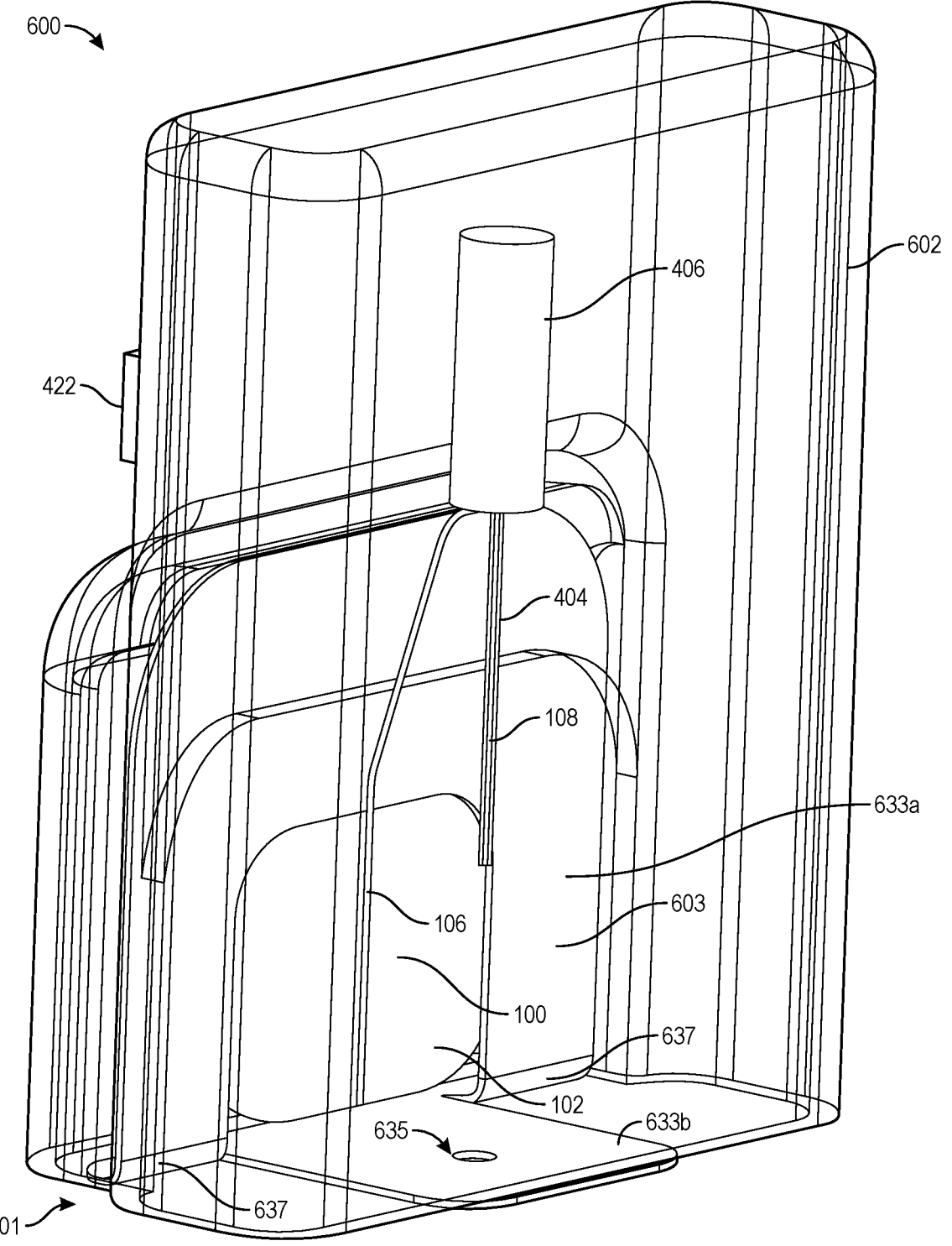
FIGS. 6A-6C show an applicator assembly configured in accordance with several embodiments of the present technology, shown in a pre-insertion state.
Figure 6B:
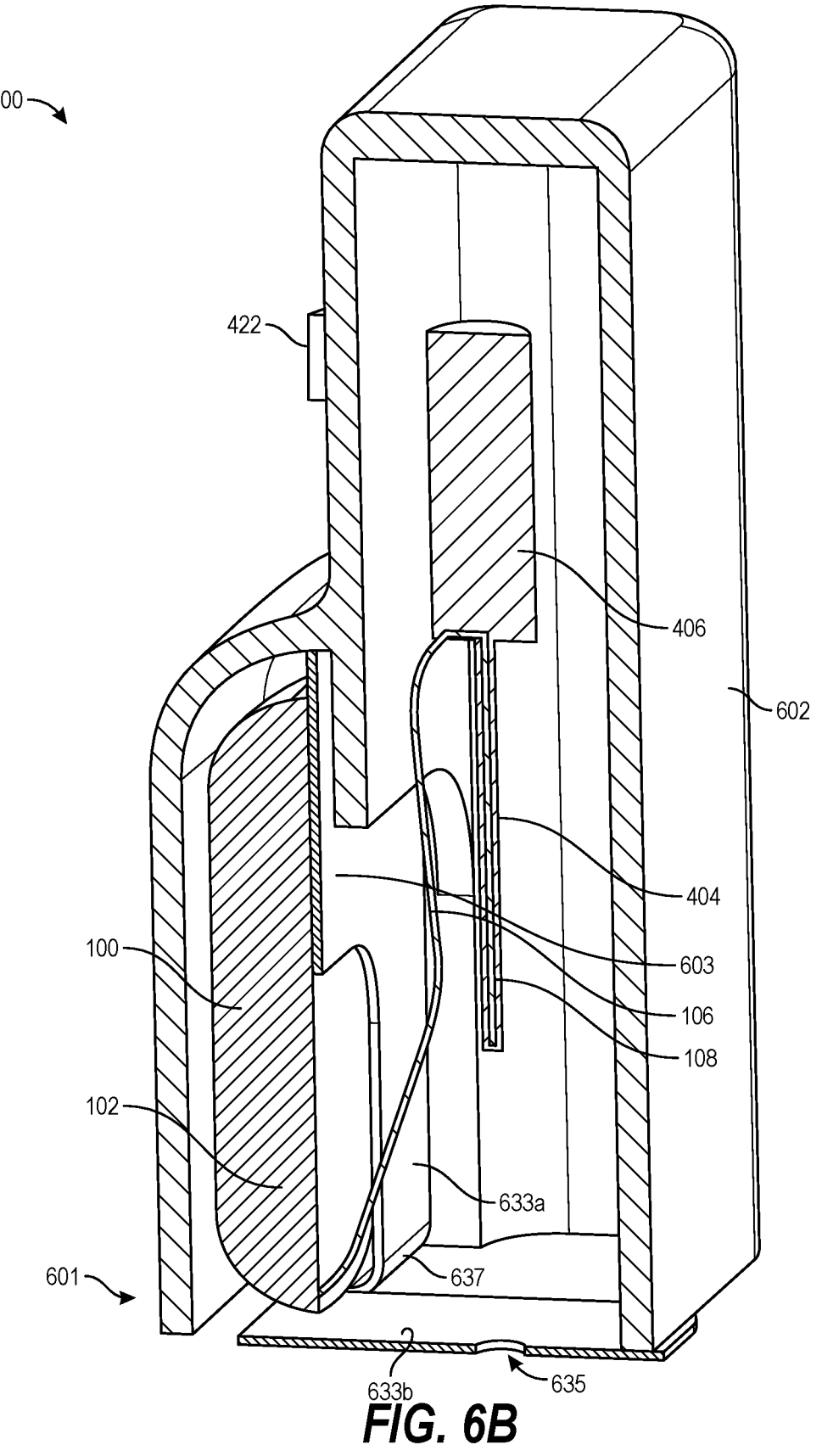
Figure 6C:
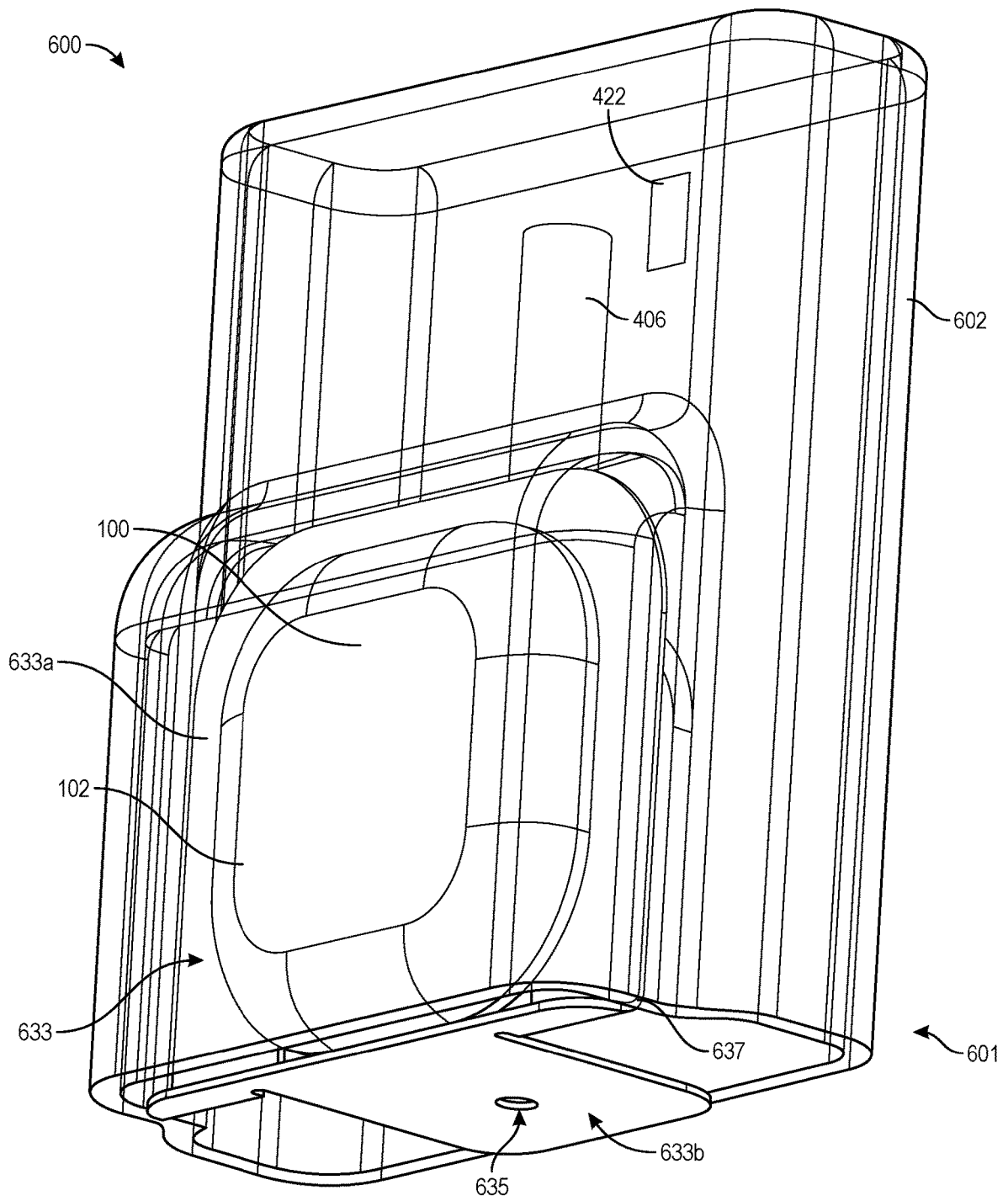

FIGS. 6A-6C are different views of an applicator assembly 600 (or "applicator 600") configured for use with the sensor assembly 100 of the present technology. Only select internal components are shown in FIGS. 6A-6C. In FIGS. 6A-6C, the applicator 600 is shown in a pre-insertion state. The applicator 600 can include a housing 602 defining an interior cavity and having an insertion end 601 configured to be positioned on or adjacent a patient's skin at an insertion site. The housing 602 can be the same as housing 402, except housing 602 may not have a cut-out in the sidewall at the insertion end 601. The housing 602 can be configured to receive a support 603 and the sensor assembly 100 within its interior cavity. The sensor assembly 100 and/or support 603 may come pre-loaded within the applicator 600, or the sensor assembly 100 and/or support 603 may be packaged separately and can be loaded by the user into the applicator 600. The applicator 600 can further include the needle 404 and the needle carrier 406 positioned within the cavity of the housing 602.

The support 603 can include first and second portions 633a, 633b that are joined to one another at a bendable portion 637. The second portion 633b includes an opening 635 that is configured to receive a needle therethrough. The support 603 is movable between a loaded configuration in which the first and second portions 633a, 633b are angled relative to one another (e.g., by greater than 45 degrees, about 90 degrees, etc.) and a wearable configuration (see FIG. 6G) in which the first and second portions 633a, 633b are aligned with one another in the same plane. In some embodiments, the first and second portions 633a, 633b are cut from a single sheet of material. When coupled to the housing 602 in the pre-insertion state, as shown in FIGS. 6A-6C, the support 603 can be in the loaded configuration with the first portion 633a positioned vertically within the interior cavity and substantially parallel to the broad side of the base 102 of the sensor assembly 100. The second portion 633b can be positioned horizontally across all or a portion of the opening at the insertion end 601 of the housing 602.

Figure 6D:
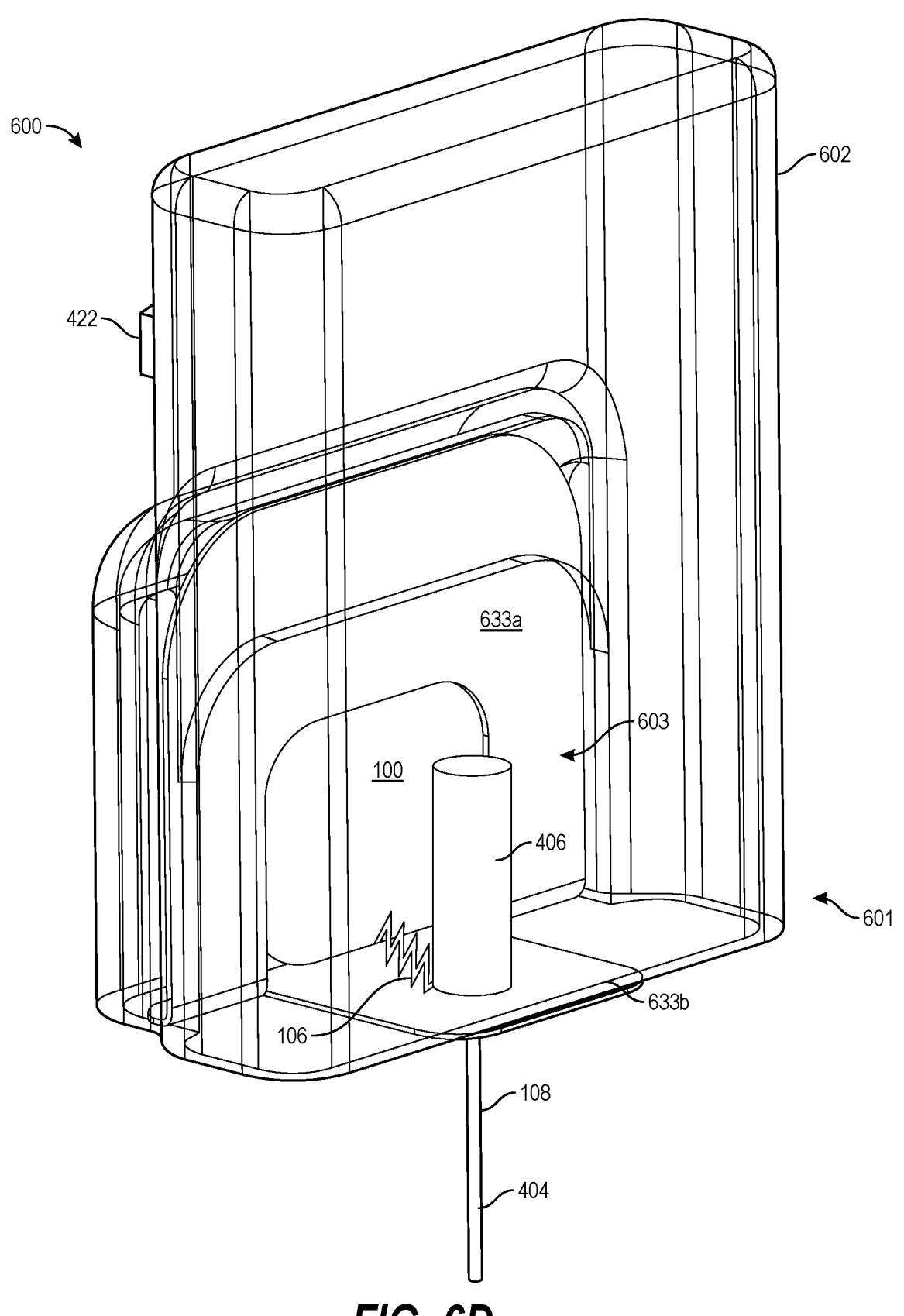
FIG. 6D shows the applicator assembly of FIGS. 6A-6C in an insertion state in accordance with several embodiments of the present technology.

FIG. 6D illustrates the applicator 600 in an insertion state in accordance with several embodiments of the present technology. In the insertion state, the needle 404 and needle carrier 406 are in an extended position in which the distal end of the needle 404 projects from the housing 602, through the opening 635 in the second portion 633b of the support 603 and into a user's skin. A user may activate insertion of the needle 404 via a trigger 422 disposed on the housing 602, a remote trigger, or other methods. The trigger may activate a first and a second spring as described above with reference to FIGS. 4A-4F. As the needle 404 moves downwardly toward the insertion site, the needle 404 brings the sensing portion 108 of the sensor 104 with it, thereby decreasing a distance between a proximal end of the extension 106 and the sensing portion 108. In response to this movement, the flexible extension 106 can be configured to bend, fold, and/or coil along its longitudinal axis to accommodate the compression in the extension 106. In some embodiments the extension 106 can accommodate such compression by folding along its longitudinal axis, similar to an accordion.

Figure 6E:
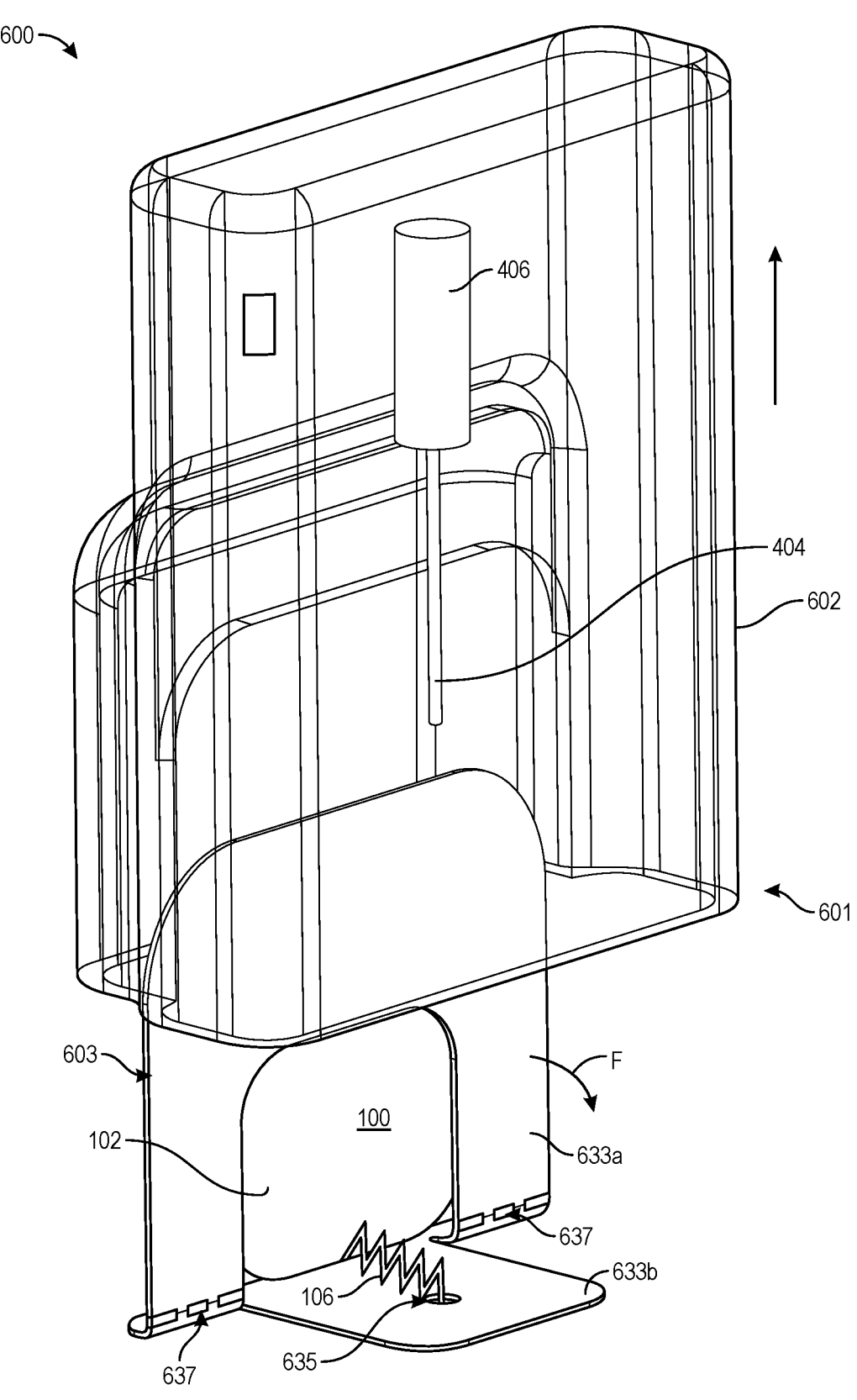
FIGS. 6E-6F show the applicator assembly of FIGS. 6A-6D as the applicator assembly is being withdrawn from the insertion site, while the sensor assembly is in an insertion position.
Figure 6F:
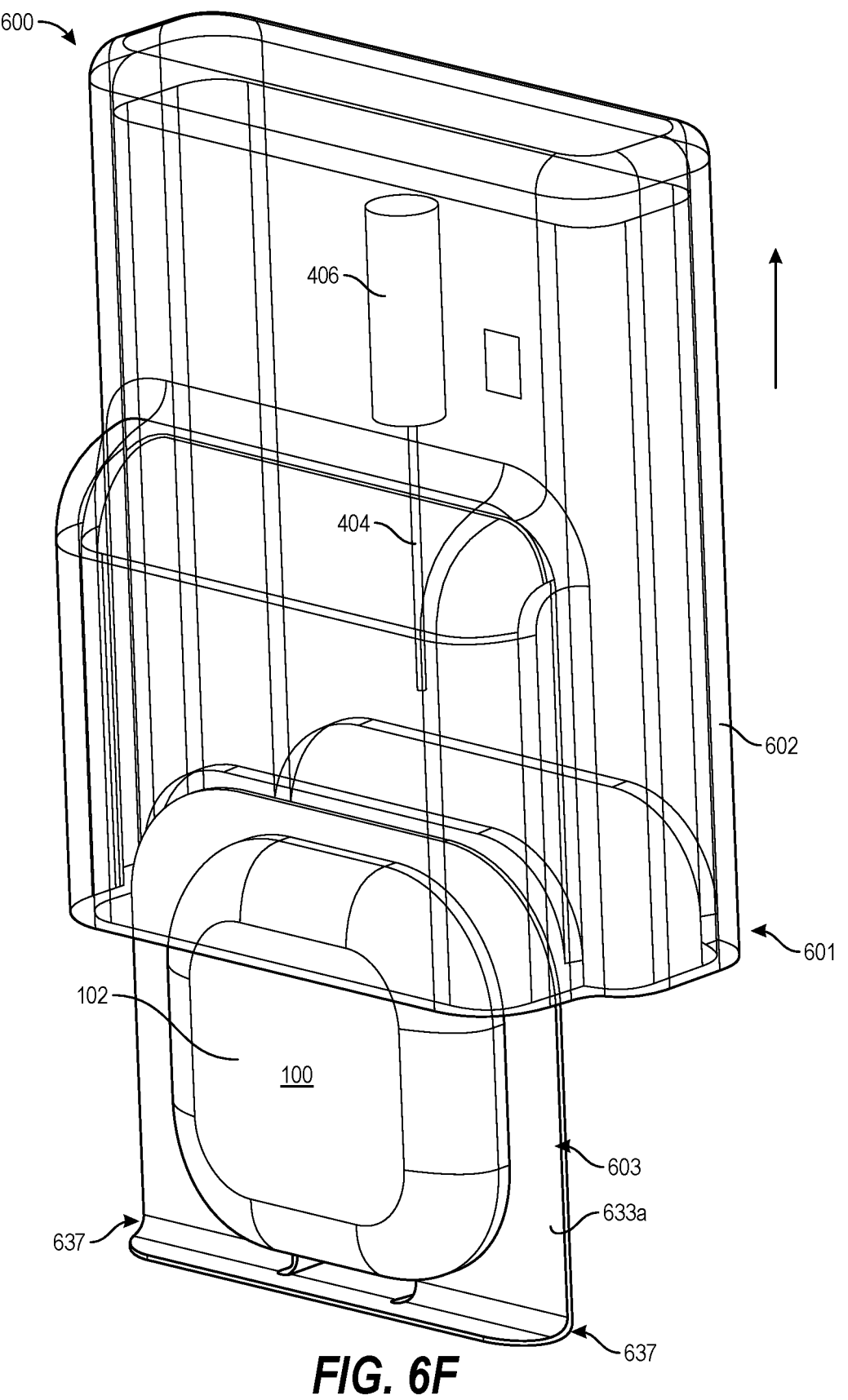

FIGS. 6E and 6F show the applicator 600 in a post-insertion state with the needle 404 in a retracted position. In some embodiments, insertion of the needle 404 can trigger the retraction assembly to retract the needle 404 into the housing 602 (e.g., by movement of the second spring as shown above), thereby leaving the sensing portion 108 behind in the user's body.

Figure 6G:
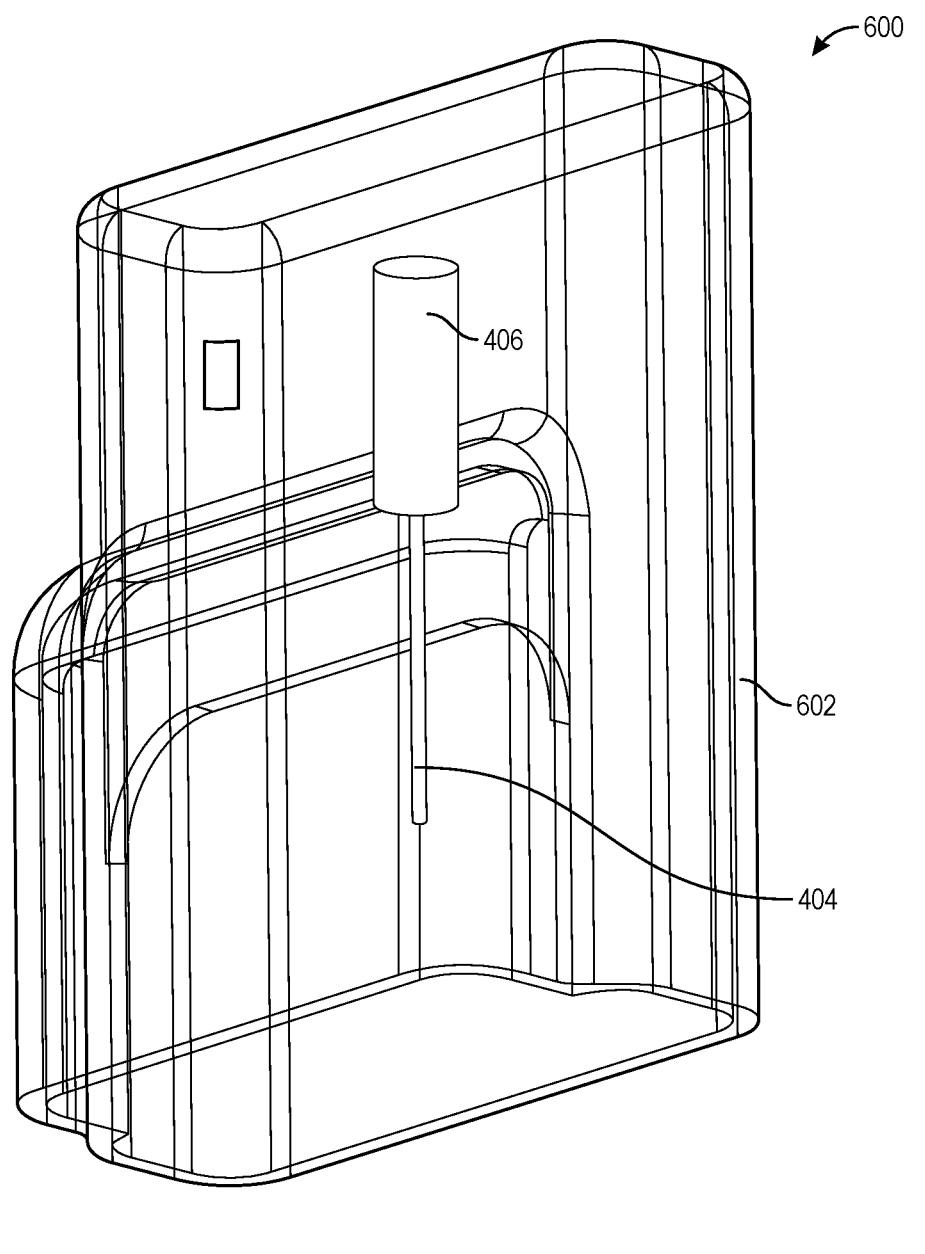
FIG. 6G shows an insertion site after the applicator assembly of FIG. 4B has been removed, leaving the sensor assembly behind in a laid-flat position.
Figure 6G:
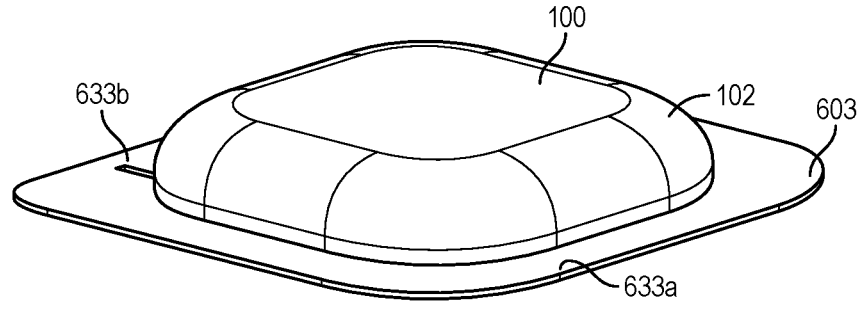

As shown in the sequence of FIGS. 6E-6G, the applicator housing 602 can then be withdrawn from the insertion site, thereby exposing the base 102 and the first portion 633*a* of the support 603 in the upright position. Removal of the housing 602 releases the tension in the bendable portion 637, thereby rotating the first portion 633*a* of the base 102 downwardly (about the bendable portion 637) towards the skin and/or second portion 633*b* of the support 603 until the first and second portions 633*a*, 633*b* are in substantially the same plane on the user's skin. Because the first portion 633*a* is adhered to the base 102, the base 102 rotates downwardly with the first portion 633*a* until the base 102 is in a laid-flat position on or adjacent the user's skin.

Figure 7A:
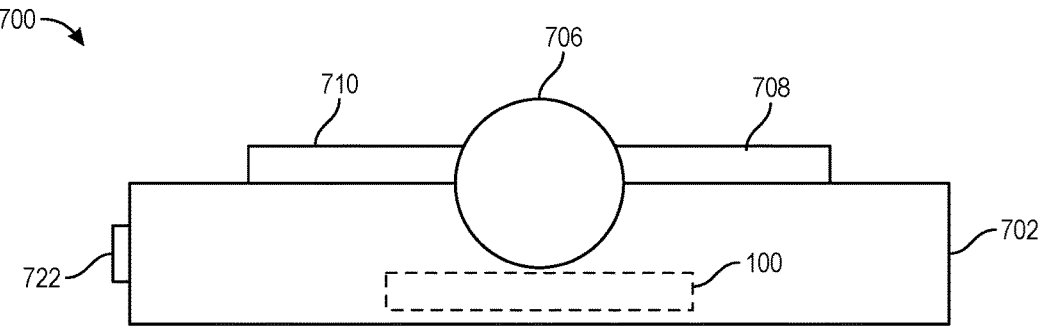
FIGS. 7A and 7B are end and top views, respectively, of an applicator assembly configured in accordance with several embodiments of the present technology, shown in a pre-insertion state.
Figure 7B:
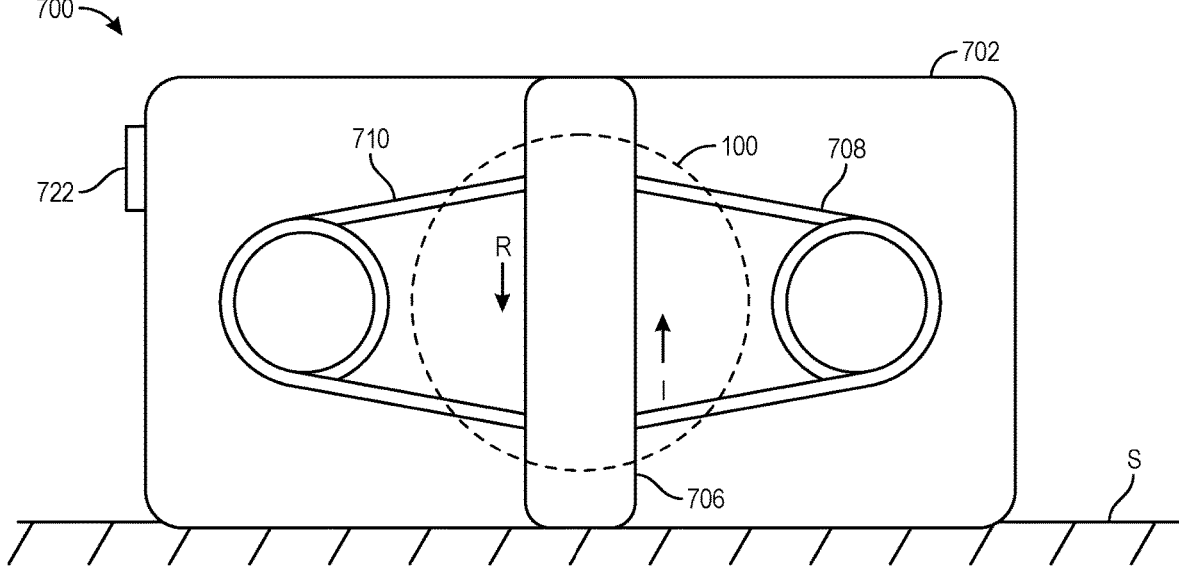

FIGS. 7A and 7B schematically depict an applicator assembly 700 (or "applicator 700") configured for use with the sensor assembly 100 of the present technology. FIG. 7A is a top view and FIG. 7B is a side view. In FIGS. 7A and 7B, the applicator 700 is shown in a pre-insertion state. The applicator 700 can include a low-profile housing 702 defining an interior cavity and having an insertion end configured to be positioned on or adjacent a patient's skin S (FIG. 7B) at an insertion site. The applicator 700 can further include a needle and a needle carrier (referred to and shown as "needle assembly 706") positioned within the cavity of the housing 702. The housing 702 can extend laterally away from the needle assembly 706 on one or both sides to provide grip support for a user.

The housing 702 can be configured to receive a sensor assembly 100 within its interior cavity. When coupled to the housing 702 in the pre-insertion state, as shown in FIGS. 7A and 7B, the sensor assembly 100 can be positioned vertically within the interior cavity and substantially parallel to the broad side of the housing 702 and/or the direction of needle insertion. After insertion, when the housing 702 is withdrawn, the sensor assembly 100 is configured to rotate downwardly onto the patient's skin S, similar to as described above in the other exemplary configurations. The applicator 700 and/or sensor assembly 100 can be configured for use with any of the supports disclosed herein.

The applicator 700 can include an insertion assembly coupled to the needle assembly 706 and configured to move the needle from a pre-insertion position within the housing 702 to an extended position in which a distal end of the needle projects relative to the housing 702. The insertion assembly can include, for example, a first torsion spring 708 coupled to the needle assembly 706 and the housing 702 (or component therein and/or thereon) and held in compression when the applicator 700 is in a pre-insertion state. When insertion is desired, a user may cause the first spring 708 to be released, thereby pushing the needle carrier downwardly towards the insertion end of the housing 702 and into the user's skin. In some embodiments, the applicator 700 further includes a retraction assembly coupled to the needle assembly 706 that is configured to move the needle from the extended position to a retracted position in which the distal end of the needle is within the housing 702. The retraction assembly can include, for example, a second torsion spring 710 coupled to the needle carrier 706 and the housing 702 (or component therein and/or thereon) and held in compression until the needle reaches the extended position. Once released, the second spring 710 pushes the needle and/or needle carrier upwardly until the sharp distal end of the needle is contained and protected by the housing 702. The use of torsion springs provides the benefit of enabling a slimmer applicator profile.

Figure 8:
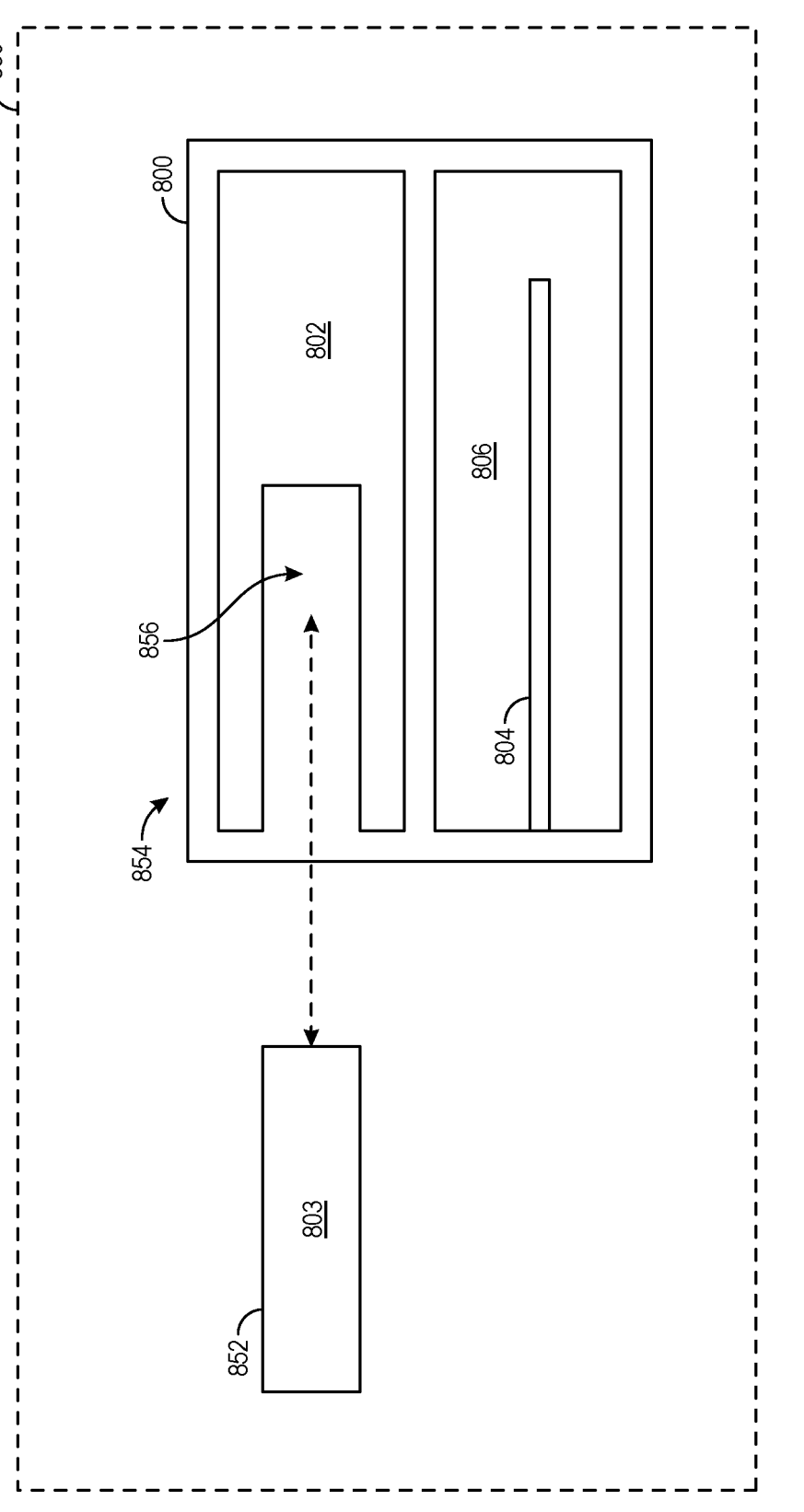
FIG. 8 schematically depicts an analyte monitoring system configured in accordance with the present technology.

As previously mentioned, the component design and arrangement of the present technology enables a lower-cost analyte monitoring system that utilizes both re-usable and disposable components. FIG. 8, for example, schematically depicts such an analyte monitoring system 850 configured in accordance with the present technology. The monitoring system 850 can comprise a reusable component 852 and a disposable component 854 that are configured to be assembled/dissembled by a user before and after use. In FIG. 8, the monitoring system 850 is shown in a dissembled state with the reusable component 852 detached from the disposable component 854. In some embodiments, the disposable component 854 comprises an applicator 800 that is pre-loaded with a needle 804 and insertion assembly 806, as well as a sensor assembly 802 devoid of certain higher-cost electronic components, such as at least one of a PCBA, an antenna, and a battery. These and/or other electronic components can be provided separately in the reusable component 852. For example, the reusable component 852 can comprise an electronics component 803 configured to be electrically coupled to the sensor assembly 802. The electronics component 803 can comprise one or more of a PCBA, an antenna, a battery, and other electronics. According to some methods of use, before deploying the applicator 800, a user can insert the reusable component 852 (indicated by the arrow in FIG. 8) into a portion of the disposable component 854 to electrically couple the electronic component 803 to the sensor assembly 802. In some embodiments, the sensor assembly 802 comprises a coupling region 856 configured to receive and/or otherwise electrically couple to a reusable electronics component. According to some methods, all or a portion of the sensor assembly 802 can be removed from the applicator 800 to allow attachment to/detachment from the reusable component 852.

CONCLUSION

Although many of the embodiments are described above with respect to systems, devices, and methods for measuring blood glucose levels and/or inserting a glucose sensor subcutaneously, the technology is applicable to other applications and/or other approaches, such as measuring non-glucose analyte levels, inserting non-glucose sensors, and/or treating medical conditions other than diabetes. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-8.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A sensor applicator comprising:
a housing having an insertion end configured to be positioned at or adjacent a user's skin at an insertion site;
a needle carried by the housing and configured for insertion into the user's skin at the insertion site; and
a sensor assembly comprising a base and a sensing portion extending from the base, the sensing portion connected to the base via an ex vivo extension having a longitudinal axis, wherein the ex vivo extension is configured to at least one of bend, fold, and/or coil along the longitudinal axis, and wherein the base is supported by the housing in a first position during insertion of the needle and configured to rotate into a second, laid-flat position on the user's skin after removal of the housing from the insertion site.

2. The applicator of claim 1, wherein the sensing portion of the sensor assembly is coupled to the needle such that subcutaneous insertion of the needle causes subcutaneous insertion of the sensing portion.

3. The applicator of claim 1, wherein the base is disposed laterally adjacent the needle such that an insertion path of the needle does not intersect any portion of the base.

4. The applicator of claim 1, wherein the needle has a distal end configured to be inserted through the user's skin, and wherein the needle is movable between a pre-insertion position in which the distal end is retracted relative to the insertion end of the housing, and an extended position in which the distal end projects relative to the insertion end.

5. The applicator of claim 1, wherein the insertion end of the applicator is configured to engage an adhesive pad positioned on the user's skin at the insertion site.

6. The applicator of claim 5, further comprising a spring configured to move the needle from a pre-insertion position within the housing to an extended position in which a distal end of the needle projects from the insertion end of the housing.

7. The applicator of claim 5, further comprising a spring configured to move the needle from an extended position in which a distal end of the needle projects from the insertion end of the housing to a retracted position in which the distal end of the needle is within the housing.

8. The applicator of claim 1, wherein, when the base is in the first position, a long axis of the base is substantially parallel to an insertion path of the needle.

9. The applicator of claim 1, wherein, when the base is in the first position, a long axis of the base is substantially perpendicular to the user's skin.

10. The applicator of claim 1, wherein the sensor assembly is configured to measure blood glucose levels after the base is rotated to the second, laid-flat position on the user's skin.

11. The applicator of claim 1, wherein the base is configured to rotate over the extension into the second, laid-flat position such that the ex vivo extension is disposed between the base and the user's skin.

12. The applicator of claim 1, wherein the applicator comprises a transmitter configured to wirelessly communicate with a remote infusion pump and/or monitor device.

13. The applicator of claim 1, wherein the sensor assembly comprises an integrated transmitter configured to wirelessly communicate with a remote infusion pump and/or monitor device.

14. The applicator of claim 1, wherein, when the base is in the first position, the base has a first end proximate the insertion end of the housing and a second end, and wherein the sensor assembly comprises a spring-loaded hinge at the first end of the base such that, when the housing is removed from the insertion site, the base automatically rotates from the first position to a second position.

15. A sensor applicator comprising:
a housing having an insertion end configured to be positioned at or adjacent a user's skin at an insertion site;
a needle carried by the housing and configured for insertion into the user's skin at the insertion site; and
a sensor assembly comprising a base and a sensing portion extending from the base, the sensing portion connected to the base via an ex vivo extension having a longitudinal axis, wherein the ex vivo extension is configured to at least one of bend, fold, and/or coil along the longitudinal axis, and the base having a first end and a second end along its long axis, wherein:
the base is supported by the housing in a first orientation during insertion of the needle in which the first end of the base is adjacent the user's skin and the second end is spaced apart from the user's skin by a distance equivalent to a length of the long axis of the base, and
the base is configured to move into a second orientation after removal of the housing from the insertion site in which both the first and second ends are adjacent the user's skin.

* * * * *